United States Patent [19]
Gerald et al.

[11] Patent Number: 5,472,866
[45] Date of Patent: Dec. 5, 1995

[54] DNA ENCODING 5-$HT_{4A}$ SEROTONIN RECEPTORS

[75] Inventors: Christophe Gerald, Ridgewood; Paul R. Hartig, Kinnelon; Theresa A. Branchek, Teaneck, all of N.J.; Richard L. Weinshank, New York, N.Y.

[73] Assignee: Synaptic Pharmaceutical Corporation, Paramus, N.J.

[21] Appl. No.: 996,772

[22] Filed: Dec. 24, 1992

[51] Int. Cl.$^6$ .................... C12N 15/00; C12N 15/12; C12N 1/00; C12N 5/00

[52] U.S. Cl. ................ 435/240.2; 536/23.5; 435/69.1; 435/252.3; 435/255.1; 435/320.1

[58] Field of Search ............... 435/6, 172.3, 240.2, 435/252.3, 69.1, 320.1, 255.1; 536/23.5

[56] References Cited

U.S. PATENT DOCUMENTS

| | | | |
|---|---|---|---|
| 4,985,352 | 1/1991 | Julius et al. | 435/6 |
| 5,242,822 | 7/1993 | Marullo et al. | 435/252.3 |

OTHER PUBLICATIONS

Loric, S., *FEBS Letters*, 312 (2–3):203–207, 1992.
Weinshank, R. L., "Molecular Analysis of Serotonin Receptor Subtypes" in *Serotonin Receptor Subtypes: Pharmacological Significance and Clinical Implications*, Langer et al. (ed.), Int. Acad. Biomed. Drug Res., Basel, Karger, 1992, vol. 1, pp. 1–12.

*Primary Examiner*—Marianne P. Allen
*Attorney, Agent, or Firm*—John P. White

[57] ABSTRACT

This invention provides an isolated nucleic acid molecule encoding a mammalian 5-$HT_{4A}$ receptor and an isolated nucleic acid molecule encoding a human 5-$HT_{4A}$ receptor, an isolated protein which is a mammalian 5-$HT_{4A}$ receptor, an isolated protein which is a human 5-$HT_{4A}$ receptor, vectors comprising an isolated nucleic acid molecule encoding a mammalian 5-$HT_{4A}$ receptor, vectors comprising an isolated nucleic acid molecule encoding a human 5-$HT_{4A}$ receptor, mammalian cells comprising such vectors, antibodies directed to the 5-$HT_{4A}$ receptor, nucleic acid probes useful for detecting nucleic acid encoding a mammalian or human 5-$HT_{4A}$ receptor, antisense oligonucleotides complementary to any sequences of a nucleic acid molecule which encodes a mammalian or human 5-$HT_{4A}$ receptor, pharmaceutical compounds related to the human 5-$HT_{4A}$ receptor, and nonhuman transgenic animals which express DNA encoding a normal or a mutant mammalian or human 5-$HT_{4A}$ receptor. This invention further provides methods for determining ligand binding, detecting expression, drug screening, and treatments for alleviating abnormalities associated with a human 5-$HT_{4A}$ receptor.

26 Claims, 12 Drawing Sheets

FIGURE 1

```
   1 AGCCTTGCCGAGCCTGGCTTGGTTGGAAGGAGGAGGATGCTCTGCGTGCCCAGGGTCCTG   60
  61 TGGGCACTGACATCCAACGTACTCATGCCCATTTCCTGTAATGGACAGACTTGATGCTAA  120
                                                    M  D  R  L  D  A  N    7
 121 TGTGAGTTCCAACGAGGGTTTCGGGTCTGTGGAGAAGGTCGTACTGCTCACGTTCTTCGC  180
   8  V  S  S  N  E  G  F  G  S  V  E  K  V  V  L  L  T  F  F  A   27
 181 AATGGTTATCCTGATGGCCATCCTGGGCAACCTGCTGGTGATGGTTGCTGTGTGCAGGGA  240
  28  M  V  I  L  M  A  I  L  G  N  L  L  V  M  V  A  V  C  R  D   47
 241 CAGGCAGCTCAGGAAAATAAAAACCAATTATTTCATTGTGTCTCTTGCCTTTGCTGATCT  300
  48  R  Q  L  R  K  I  K  T  N  Y  F  I  V  S  L  A  F  A  D  L   67
 301 GCTGGTTTCGGTGCTGGTGAATGCCTTCGGTGCCATTGAGTTGGTCCAAGACATCTGGTT  360
  68  L  V  S  V  L  V  N  A  F  G  A  I  E  L  V  Q  D  I  W  F   87
 361 TTATGGGGagatgttttgcctggtccggacctctctggatgtcctactcaccacagcatc  420
  88  Y  G  E  M  F  C  L  V  R  T  S  L  D  V  L  L  T  T  A  S  107
 421 aattttcacctctgctgcatttcccTGGATAGGTATTATGCCATCTGCTGTCAACCTTT  480
 108  I  F  H  L  C  C  I  S  L  D  R  Y  Y  A  I  C  C  Q  P  L  127
 481 GGTTTATAGAAACAAGATGACCCCTCTACGCATCGCATTAATGCTGGGAGGCTGCTGGGT  540
 128  V  Y  R  N  K  M  T  P  L  R  I  A  L  M  L  G  G  C  W  V  147
 541 CATTCCCATGTTTATATCTTTTCTCCCCATAATGCAAGGCTGGAACAACATCGGCATAGT  600
 148  I  P  M  F  I  S  F  L  P  I  M  Q  G  W  N  N  I  G  I  V  167
 601 TGATGTGATAGAGAAAAGGAAATTCAACCACAACTCTAACTCTACATTCTGTGTCTTCAT  660
 168  D  V  I  E  K  R  K  F  N  H  N  S  N  S  T  F  C  V  F  M  187
 661 GGTCAACAAGCCCTATGCCATCACCTGCTCTGTGGTGGCCTTCTACATCCCGTTTCTCCT  720
 188  V  N  K  P  Y  A  I  T  C  S  V  V  A  F  Y  I  P  F  L  L  207
 721 CATGGTGCTGGCCTATTACCGTATCTATGTCACTGCTAAGGAGCATGCCCAGCAGATCCA  780
 208  M  V  L  A  Y  Y  R  I  Y  V  T  A  K  E  H  A  Q  Q  I  Q  227
 781 GATGTTACAACGGGCAGGAGCCACCTCTGAAAGCAGGCCCCAGACAGCTGACCAGCACAG  840
 228  M  L  Q  R  A  G  A  T  S  E  S  R  P  Q  T  A  D  Q  H  S  247
 841 CACACATCGCATGCGGACAGAGACCAAAGCAGCCAAGACTTTATGTGTCATCATGGGCTG  900
 248  T  H  R  M  R  T  E  T  K  A  A  K  T  L  C  V  I  M  G  C  267
 901 CTTCTGTTTCTGCTGGGCCCCCTTCTTTGTCACCAATATTGTGGACCCTTTCATAGACTA  960
 268  F  C  F  C  W  A  P  F  F  V  T  N  I  V  D  P  F  I  D  Y  287
 961 CACTGTGCCCGAGAAGGTGTGGACTGCTTTCCTCTGGCTTGGCTATATCAATTCAGGGTT 1020
 288  T  V  P  E  K  V  W  T  A  F  L  W  L  G  Y  I  N  S  G  L  307
1021 GAACCCTTTTCTCTATGCCTTCTTGAATAAGTCTTTCAGACGTGCCTTCCTTATCATCCT 1080
 308  N  P  F  L  Y  A  F  L  N  K  S  F  R  R  A  F  L  I  I  L  327
1081 CTGCTGTGATGATGAGCGCTACAAAAGACCCCCCATTCTGGGCCAGACTGTCCCCTGTTC 1140
 328  C  C  D  D  E  R  Y  K  R  P  P  I  L  G  Q  T  V  P  C  S  347
1141 AACCACAACCATTAATGGATCCACTCATGTGCTAAGGTATACAGTTTTGCATAGTGGTCA 1200
 348  T  T  T  I  N  G  S  T  H  V  L  R  Y  T  V  L  H  S  G  Q  367
1201 ACACCAGGAACTGGAGAAGTTGCCCATACACAATGACCCAGAGTCCCTGGAATCATGCTT 1260
 368  H  Q  E  L  E  K  L  P  I  H  N  D  P  E  S  L  E  S  C  F  387
1261 TTGATTGAAGACGTGGCTTGCCTTTAGCGGTTCATCCCATCTGTGTCTGCATGAACAGGT 1320
        *
1321 TACTATGGAATCACTCCTGACTCTGGGCATCACCAGTGAAGCATGAGCATGGTGAGGCAG 1380
1381 GGTCCGGTGAAGGTGCACAGAGGACAGCATTGAGTGGGACCTGAACCCAGCACATTAAGG 1440
1441 ATTTCAGAACCGTGTGGGGATTTGAGATGTCATCAGACCCAGTGTCTTACCCAGAGCCCA 1500
1501 ACTGGCACCTCCCATTCCACGCTGACATGTGGTCAGTCTTTGCTCACACCTCTCCAGGGG 1560
1561 CAGGAGCTGACTACCTCCTAATGTGGTGGGGAGCTCTTAATTGTGTGGAAGTTCAGTCAT 1620
1621 TCATTGGTGGACAGTCTCGCTG 1642
```

FIGURE 2

```
   1                                   AGGGTCCTGTGGGCACTGACATCCAACGTACTCA    34
  35 TGCCCATTTCCTGTAATGGACAGACTTGATGCTAATGTGAGTTCCAACGAGGGTTTCGGG            94
                      M  D  R  L  D  A  N  V  S  S  N  E  G  F  G           15
  95 TCTGTGGAGAAGGTCGTACTGCTCACGTTCTTCGCAATGGTTATCCTGATGGCCATCCTG           154
  16  S  V  E  K  V  V  L  L  T  F  F  A  M  V  I  L  M  A  I  L            35
 155 GGCAACCTGCTGGTGATGGTTGCTGTGTGCAGGGACAGGCAGCTCAGGAAAATAAAAACC           214
  36  G  N  L  L  V  M  V  A  V  C  R  D  R  Q  L  R  K  I  K  T            55
 215 AATTATTTCATTGTGTCTCTTGCCTTTGCTGATCTGCTGGTTTCGGTGCTGGTGAATGCC           274
  56  N  Y  F  I  V  S  L  A  F  A  D  L  L  V  S  V  L  V  N  A            75
 275 TTCGGTGCCATTGAGTTGGTCCAAGACATCTGGTTTTATGGGGAGATGTTTTGCCTGGTC           334
  76  F  G  A  I  E  L  V  Q  D  I  W  F  Y  G  E  M  F  C  L  V            95
 335 CGGACCTCTCTGGATGTCCTACTCACCACAGCATCAATTTTTCACCTCTGCTGCCTTTCC           394
  96  R  T  S  L  D  V  L  L  T  T  A  S  I  F  H  L  C  C  I  S           115
 395 CTGGATAGGTATTATGCCATCTGCTGTCAACCTTTGGTTTATAGAAACAAGATGACCCCT           454
 116  L  D  R  Y  Y  A  I  C  C  Q  P  L  V  Y  R  N  K  M  T  P           135
 455 CTACGCATCGCATTAATGCTGGGAGGCTGCTGGGTCATTCCCATGTTTATATCTTTTCTC           514
 136  L  R  I  A  L  M  L  G  G  C  W  V  I  P  M  F  I  S  F  L           155
 515 CCCATAATGCAAGGCTGGAACAACATCGGCATAGTTGATGTGATAGAGAAAAGGAAATTC           574
 156  P  I  M  Q  G  W  N  N  I  G  I  V  D  V  I  E  K  R  K  F           175
 575 AACCACAACTCTAACTCTACATTCTGTGTCTTCATGGTCAACAAGCCCTATGCCATCACC           634
 176  N  H  N  S  N  S  T  F  C  V  F  M  V  N  K  P  Y  A  I  T           195
 635 TGCTCTGTGGTGGCCTTCTACATCCCGTTTCTCCTCATGGTGCTGGCCTATTACCGTATC           694
 196  C  S  V  V  A  F  Y  I  P  F  L  L  M  V  L  A  Y  Y  R  I           215
 695 TATGTCACTGCTAAGGAGCATGCCCAGCAGATCCAGATGTTACAACGGGCAGGAGCCACC           754
 216  Y  V  T  A  K  E  H  A  Q  Q  I  Q  M  L  Q  R  A  G  A  T           235
 755 TCTGAAAGCAGGCCCCAGACAGCTGACCAGCACAGCACACATCGCATGCGGACAGAGACC           814
 236  S  E  S  R  P  Q  T  A  D  Q  H  S  T  H  R  M  R  T  E  T           255
 815 AAAGCAGCCAAGACTTTATGTGTCATCATGGGCTGCTTCTGTTTCTGCTGGGCCCCCTTC           874
 256  K  A  A  K  T  L  C  V  I  M  G  C  F  C  F  C  W  A  P  F           275
 875 TTTGTCACCAATATTGTGGACCCTTTCATAGACTACACTGTGCCCGAGAAGGTGTGGACT           934
 276  F  V  T  N  I  V  D  P  F  I  D  Y  T  V  P  E  K  V  W  T           295
 935 GCTTTCCTCTGGCTTGGCTATATCAATTCAGGGTTGAACCCTTTTCTCTATGCCTTCTTG           994
 296  A  F  L  W  L  G  Y  I  N  S  G  L  N  P  F  L  Y  A  F  L           315
 995 AATAAGTCTTTCAGACGTGCCTTCCTTATCATCCTCTGCTGTGATGATGAGCGCTACAAA          1054
 316  N  K  S  F  R  R  A  F  L  I  I  L  C  C  D  D  E  R  Y  K           335
1055 AGACCCCCCATTCTGGGCCAGACTGTCCCCTGTTCAACCACAACCATTAATGGATCCACT          1114
 336  R  P  P  I  L  G  Q  T  V  P  C  S  T  T  T  I  N  G  S  T           355
1115 CATGTGCTAAGGGATACAGTGGAATGTGGTGGCCAATGGGAGAGTCGGTGTCACCTCACA          1174
 356  H  V  L  R  D  T  V  E  C  G  G  Q  W  E  S  R  C  H  L  T           375
1175 GCAACTTCTCCTTTGGTGGCTGCTCAGCCAGTGATACGTAGGCCCCAGGACAATGACCTA          1234
 376  A  T  S  P  L  V  A  A  Q  P  V  I  R  R  P  Q  D  N  D  L           395
1235 GAAGACAGCTGTAGCTTGAAAAGAAGCCAGTCCTAAGCTGCTACTTCGGTGTATGTGGCT          1294
 396  E  D  S  C  S  L  K  R  S  Q  S  *                                   406
1295 GCCCCTGGCACTTTGTTCTCCAAGGCTTTCCAAGAGCATGAGGCAATCCACCCTGGACTT          1354
1355 CCCGCCACGATTCTAGCAGGCGGTATTAGAGGAAGTCAGGGGAGAGAAGGGCTTCCTCCT          1414
1415 TAGCTTTCTGTTTCTCAACATTTTCTCTTCCTGGAGTCTCCACTCTTGCTTGGTGGTCTC          1474
1475 TGAAGTCCACGACCCAGTCCCCTTTTGCTGTCTCCAGTCTGTCTTGTAAATGTTTACCGT          1534
1535 GTTCGATTTTCAGTTTCCAAACATGCCTTCTTTGAAGTGTCATCTTACGATACTGTCAAA          1594
1595 ACATGTGCCTGTCTTGATCACACTTCTT
```

FIGURE 3

```
1   MDRLDANVSSNEGFGSVEKVVLLTFFAMVILMAILGNLLVMVAVCRDRQL  50
    ||||||||||||||||||||||||||||||||||||||||||||||||||
1   MDRLDANVSSNEGFGSVEKVVLLTFFAMVILMAILGNLLVMVAVCRDRQL  50

51  RKIKTNYFIVSLAFADLLVSVLVNAFGAIELVQDIWFYGEMFCLVRTSLD  100
    ||||||||||||||||||||||||||||||||||||||||||||||||||
51  RKIKTNYFIVSLAFADLLVSVLVNAFGAIELVQDIWFYGEMFCLVRTSLD  100

101 VLLTTASIFHLCCISLDRYYAICCQPLVYRNKMTPLRIALMLGGCWVIPM  150
    ||||||||||||||||||||||||||||||||||||||||||||||||||
101 VLLTTASIFHLCCISLDRYYAICCQPLVYRNKMTPLRIALMLGGCWVIPM  150

151 FISFLPIMQGWNNIGIVDVIEKRKFNHNSNSTFCVFMVNKPYAITCSVVA  200
    ||||||||||||||||||||||||||||||||||||||||||||||||||
151 FISFLPIMQGWNNIGIVDVIEKRKFNHNSNSTFCVFMVNKPYAITCSVVA  200

201 FYIPFLLMVLAYYRIYVTAKEHAQQIQMLQRAGATSESRPQTADQHSTHR  250
    ||||||||||||||||||||||||||||||||||||||||||||||||||
201 FYIPFLLMVLAYYRIYVTAKEHAQQIQMLQRAGATSESRPQTADQHSTHR  250

251 MRTETKAAKTLCVIMGCFCFCWAPFFVTNIVDPFIDYTVPEKVWTAFLWL  300
    ||||||||||||||||||||||||||||||||||||||||||||||||||
251 MRTETKAAKTLCVIMGCFCFCWAPFFVTNIVDPFIDYTVPEKVWTAFLWL  300

301 GYINSGLNPFLYAFLNKSFRRAFLIILCCDDERYKRPPILGQTVPCSTTT  350
    ||||||||||||||||||||||||||||||||||||||||||||||||||
301 GYINSGLNPFLYAFLNKSFRRAFLIILCCDDERYKRPPILGQTVPCSTTT  350

351 INGSTHVLRYTVLHSGQ............HQELEKLPIHNDPESLES  385
    |||||||||  ||  :||           |.: : | .|| |  :|
351 INGSTHVLRDTVECGGQWESRCHLTATSPLVAAQPVIRRPQDNDLE..DS  398

386 CF 387
     |
399 CSLKRSQS 406
```

FIGURE 4A

| FIGURE 4A |
|---|
| FIGURE 4B |
| FIGURE 4C |

```
427  TTGGTCTATAGGAACAAGATGACCCCTCTGCGCATTAATGCTGGGAGGCTGCTGG     487
127    L  V  Y  R  N  K  M  T  P  L  R  I  A  L  M  L  G  G  C  W      146
488  GTCATCCCCACGTTTATTTCTTTTCCCTATAATGCAAGGCTGGAATAACATTGGCATA  547
147    V  I  P  T  F  I  S  F  L  P  I  M  Q  G  W  N  N  I  G  I      166
548  ATTGATTTGATAGAAAAGAGGAAGTTCAACCAGAACTCTACGTACTGTGTCTTC       607
167    I  D  L  I  E  K  R  K  F  N  Q  N  S  N  S  T  Y  C  V  F      186
608  ATGGTCAACAAGCCCTACGCCATCACCTGCTCTGTGGTGGCCTTCTACATCCCATTTCTC 667
187    M  V  N  K  P  Y  A  I  T  C  S  V  V  A  F  Y  I  P  F  L      206
668  CTCATGGTGCTGGCCTATTACCGCATCTATGTCACAGCTAAGGAGCATGCCCATCAGATC 727
207    L  M  V  L  A  Y  Y  R  I  Y  V  T  A  K  E  H  A  H  Q  I      226
728  CAGATGTTACAACGGGCAGGAGCCTCCTCCGAGAGCAGGCCTCAGTCGGCAGACCAGCAT 787
227    Q  M  L  Q  R  A  G  A  S  S  E  S  R  P  Q  S  A  D  Q  H      246
788  AGCACTCATCCGATGAGGACAGAGACCAAAGCAGCCAAGACCCTGTGCATCATCATGGGT 847
247    S  T  H  P  M  R  T  E  T  K  A  K  T  L  C  I  I  M  G      266
848  TGCTTCTGCCTCTGCTGGGCACCATTCTTTGTCACCAATATTGTGGATCCTTTCATAGAC 907
267    C  F  C  L  C  W  A  P  F  F  V  T  N  I  V  D  P  F  I  D      286
908  TACACTGTCCCTGGGCAGGTGTGGACTGCTTTCCTCTGGCTCGGCTATATCAATTC     963
287    Y  T  V  P  G  Q  V  W  T  A  F  L  W  L  G  Y  I  N           304
```

FIGURE 6

```
427  TTGGTCTATAGGAACAAGATGACCCCTCTGCGCATTAATGCTGGGAGGCTGCTGG   487
          T      A
488  GTCATCCCCACGTTTATTTCTTTTCTCCCTATAATGCAAGGCTGGAATAACATTGGCATA   547
          T    T    A           C             C
548  ATTGATTTGATAGAAAAGAGGAAGTTCAACCAGAACTCTAACTCTACGTACTGTGTCTTC   607
     G       G     G    A    C                   A T
608  ATGGTCAACAAGCCCTACGCCATCACCTGCTCTGTGGTGGCCCTTCTACATCCCATTTCTC   667
                                T                           G
668  CTCATGGTGCTGGCCCTATTACCGCATCTATGTCACAGCTAAGGAGCATGCCCATCAGATC   727
                                  T                           G
728  CAGATGTTACAACGGGCAGGAGCCCTCCTCCCGAGAGCAGGCCCTCAGTCGGCAGACCAGCAT   787
                             A  T    C   A A T       C
788  AGCACTCATCCGATGAGGACAGAGACCAGCAAAGCCAAGACCCTGTGCATCATCATGGGT   847
         A  GC  C                                      TT A  TG   C
848  TGCTTCTGCCCTCTGCTGGGCACCATTCTTTGTCACCAATATTGTGGATCCTTTCATAGAC   907
        TT         C C                           C
908  TACACTGTCCCTGGGCAGGTGTGGGACTGCTTTCCCTCTGGCTCGGGCTATATCAATTC   963
        G  C A A                                T
```

FIGURE 7

```
127  LVYRNKMTPLRIALMLGGCWVIPTFISFLPIMQGWNNIGIIDLIEKRKFNQNSNSTYCVF  186
                     M                        V V        H   F
187  MVNKPYAITCSVVAFYIPFLLMVLAYYRIYVTAKEHAHQIQMLQRAGASSESRPQSADQH  246
                                            Q          T  T
247  STHPMRTETKAAKTLCIIMGCFCLCWAPFFVTNIVDPFIDYTVPGQVWTAFLWLGYIN   304
     R                V         F                EK
```

Dose Response Curve for 5-HT Stimulation of Adenylate Cyclase in CG8 Transfected COS-7 Cells

1

DNA ENCODING 5-HT$_{4A}$ SEROTONIN RECEPTORS

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Molecular cloning efforts have provided primary amino acid sequence and signal transduction data for a large collection of serotonin receptor subtypes. These include five cloned 5-HT$_1$-like receptors, three cloned 5-HT$_2$ receptors, and one 5-HT$_3$ receptor. The 5-HT$_1$ subfamily includes: 5-HT$_{1A}$ (Fargin, 1988; Kobilka, 1989), 5-HT$_{1B}$/5-HT$_{1D\beta}$ (Weinshank et al., 1991; Demchyshyn et al., 1992; Jin et al., 1992; Adham et al., 1992; Maroteaux et al., 1992; Voight et al., 1991), 5-HT$_{1D\alpha}$ (Branchek et al. 1991; Hamblin and Metcalf, 1991; Weinshank et al., 1992), 5-HT$_{1E}$ (Levy et al., 1992; McAllister et al., 1992; Zgombick et al., 1992) and 5-HT$_{1F}$ (Adham et al., 1993). All five have been shown to couple to the inhibition of adenylate cyclase activity. The 5-HT$_2$ family includes the 5-HT$_2$ receptor (Pritchett et al., 1988), 5-HT$_{1C}$ (Julius et al., 1989) and 5-HT$_{2F}$ (Rat Stomach Fundus; Foquet et al., 1992; Kursar et al., 1992). These receptors all couple to phosphoinositide hydrolysis. The 5-HT$_3$ receptor is a ligand-gated ion channel (Maricq et al., 1991).

Although this work represents enormous success, the absence of molecular biological information on the 5-HT$_4$ receptors, which have been shown in native tissues to couple to the activation of adenylate cyclase as a primary mode of signal transduction (Dumius et al., 1988; Bockaert et al., 1990), is apparent. In a previous copending application (U.S. Ser. No., 971,690, filed Nov. 3, 1992), we reported the cloning of the first mammalian 5-HT receptor that couples to the stimulation of adenylate cyclase activity which we named 5-HT$_{4B}$. The pharmacological properties of this receptor indicated that it was similar to a series of functionally defined 5-HT receptors described in the porcine vena cava (Trevethick et al., 1984), cat saphenous vein, coronary arteries (Cushing and Cohen, 1992), and several vascular dilatory effects (Mylecharane and Phillips, 1989). However, the classically defined 5-HT$_4$ receptor remained to be cloned. We now report the cloning of the pharmacologically-defined 5-HT$_4$ receptor which we have called 5-HT$_{4A}$. This receptor also stimulates adenylate cyclase activity but unlike 5-HT$_{4B}$, is sensitive to a series of benzamide derivatives which act as agonists or partial agonists at this subtype. The presence of this subtype in the brain, particularly in areas such as the hippocampus, indicates a potential role in cognitive enhancement. In addition, the 5-HT$_4$ receptor has been described functionally in the heart, adrenal, bladder, and alimentary canal indicating potential roles in achalasia, hiatal hernia, esophageal spasm, irritable bowel disease, postoperative ileus, diabetic gastroparesis, emesis and other diseases of the gastrointestinal tract, as well as in cardiac, urinary, and endocrine function.

SUMMARY OF THE INVENTION

This invention provides an isolated nucleic acid molecule encoding a mammalian 5-HT$_{4A}$ receptor. In a preferred embodiment of this invention, the isolated nucleic acid encodes a human 5-HT$_{4A}$ receptor. In another embodiment of this invention, the nucleic acid molecule encoding a human 5-HT$_{4A}$ receptor comprises a plasmid designated pBluescript-hS10 (ATCC Accession No. 75392). In another embodiment of this invention a nucleic acid molecule encoding a mammalian 5-HT$_{4A}$ receptor comprises a plasmid designated pcEXV-S10-87 (ATCC Accession No. 75390). In another embodiment of this invention a nucleic acid molecule encoding a mammalian 5-HT$_{4A}$ receptor comprises a plasmid designated pcEXV-S10-95 (ATCC Accession No. 75391).

This invention provides a nucleic acid probe comprising a nucleic acid molecule of at least 15 nucleotides capable of specifically hybridizing with a sequence included within the sequence of a nucleic acid molecule encoding a mammalian 5-HT$_{4A}$ receptor. This invention also provides a nucleic acid molecule of at least 15 nucleotides capable of specifically hybridizing with a sequence included within the sequence of a nucleic acid molecule encoding a human 5-HT$_{4A}$ receptor.

This invention provides an antisense oligonucleotide having a sequence capable of binding specifically to an mRNA molecule encoding a mammalian 5-HT$_{4A}$ receptor so as to prevent translation of the mRNA molecule. This invention also provides an antisense oligonucleotide having a sequence capable of binding specifically to an mRNA molecule encoding a human 5-HT$_{4A}$ receptor so as to prevent translation of the mRNA molecule.

This invention provides a monoclonal antibody directed to a mammalian 5-HT$_{4A}$ receptor. This invention also provides a monoclonal antibody directed to a human 5-HT4A receptor.

This invention provides a pharmaceutical composition comprising an amount of a substance effective to alleviate the abnormalities resulting from overexpression of a mammalian 5-HT$_{4A}$ receptor and a pharmaceutically acceptable carrier. This invention also provides a pharmaceutical composition comprising an amount of a substance effective to alleviate abnormalities resulting from underexpression of mammalian 5-HT$_{4A}$ receptor and a pharmaceutically acceptable carrier.

This invention provides a pharmaceutical composition comprising an amount of a substance effective to alleviate the abnormalities resulting from overexpression of a human 5-HT$_{4A}$ receptor and a pharmaceutically acceptable carrier. This invention also provides pharmaceutical composition comprising an amount of a substance effective to alleviate abnormalities resulting from underexpression of a human 5-HT$_{4A}$ receptor and a pharmaceutically acceptable carrier.

This invention provides a transgenic, nonhuman mammal whose genome comprises DNA encoding a mammalian 5-HT$_{4A}$ receptor so positioned within such genome as to be transcribed into antisense mRNA complementary to mRNA encoding the mammalian 5-HT$_{4A}$ receptor and when hybridized to mRNA encoding the mammalian 5-HT$_{4A}$ receptor, the complementary mRNA reduces the translation of the mRNA encoding the mammalian 5-HT$_{4A}$ receptor.

This invention also provides a transgenic, nonhuman mammal whose genome comprises DNA encoding a human 5-HT$_{4A}$ so positioned within such genome as to be transcribed into antisense mRNA complementary to mRNA encoding the human 5-HT$_{4A}$ and when hybridized to mRNA encoding the human 5-HT$_{4A}$, the complementary mRNA reduces the translation of the mRNA encoding the human 5-HT$_{4A}$.

This invention provides a transgenic, nonhuman mammal whose genome comprises DNA encoding a mammalian 5-HT$_{4A}$ receptor so positioned within such genome as to be transcribed into antisense mRNA which is complementary to mRNA encoding the mammalian 5-HT$_{4A}$ receptor and when hybridized to mRNA encoding the 5-HT$_{4A}$ receptor, the antisense mRNA thereby prevents the translation of mRNA encoding the 5-HT$_{4A}$ receptor.

This invention also provides a transgenic, nonhuman mammal whose genome comprises DNA encoding a human 5-HT$_{4A}$ receptor so positioned within such genome as to be transcribed into antisense mRNA which is complementary to mRNA encoding the human 5-HT$_{4A}$ receptor and when hybridized to mRNA encoding the human 5-HT$_{4A}$ receptor, the antisense mRNA thereby prevents the translation of mRNA encoding the human 5-HT$_{4A}$ receptor.

This invention also provides a method of determining the physiological effects of expressing varying levels of a mammalian 5-HT$_{4A}$ receptor which comprises producing a transgenic nonhuman animal whose levels of mammalian 5-HT$_{4A}$ receptor expression are varied by use of an inducible promoter which regulates mammalian 5-HT$_{4A}$ receptor expression.

This invention also provides a method of determining the physiological effects of expressing varying levels of a human 5-HT$_{4A}$ receptor which comprises producing a transgenic nonhuman animal whose levels of human 5-HT$_{4A}$ receptor expression are varied by use of an inducible promoter which regulates human 5-HT$_{4A}$ receptor expression.

This invention further provides a method of determining the physiological effects of expressing varying levels of mammalian 5-HT$_{4A}$ receptor which comprises producing a panel of transgenic nonhuman animals each expressing a different amount of mammalian 5-HT$_{4A}$ receptor.

This invention further provides a method of determining the physiological effects of expressing varying levels of human 5-HT$_{4A}$ receptor which comprises producing a panel of transgenic nonhuman animals each expressing a different amount of human 5-HT$_{4A}$ receptor.

This invention provides a method for determining whether a compound not known to be capable of specifically binding to a human 5-HT$_{4A}$ receptor can specifically bind to the human 5-HT$_{4A}$ receptor, which comprises contacting a mammalian cell comprising a plasmid adapted for expression in a mammalian cell which plasmid further comprises a DNA which expresses a human 5-HT$_{4A}$ receptor on the cell's surface with the compound under conditions permitting binding of ligands known to bind to a human 5-HT$_{4A}$ receptor, detecting the presence of any compound bound to the human 5-HT$_{4A}$ receptor, the presence of bound compound indicating that the compound is capable of specifically binding to the human 5-HT$_{4A}$ receptor.

This invention provides a method of screening drugs to identify drugs which interact with, and specifically bind to, a human 5-HT$_{4A}$ receptor on the surface of a cell, which comprises contacting a mammalian cell which comprises a plasmid adapted for expression in a mammalian cell which plasmid further comprises DNA which expresses a human 5-HT$_{4A}$ receptor on the cell's surface with a plurality of drugs, determining those drugs which bind to the human 5-HT$_{4A}$ receptor expressed on the cell surface of the mammalian cell, and thereby identifying drugs which interact with, and specifically bind to, the human 5-HT$_{4A}$ receptor.

This invention provides a method for identifying a compound which specifically binds to and activates or blocks the activation of a human 5-HT$_{4A}$ receptor on the surface of a mammalian cell, which comprises contacting the mammalian cell which comprises a plasmid adapted for expression in the mammalian cell such plasmid further comprising DNA which expresses the human 5-HT$_{4A}$ receptor on the cell surface of the mammalian cell with the compound, determining whether the compound activates or blocks the activation of the human 5-HT$_{4A}$ receptor and thereby identifying the compound as a compound which binds to, and activates or blocks the activation of the human 5-HT$_{4A}$ receptor.

This invention provides a method for diagnosing a predisposition to a disorder associated with the expression of a human 5-HT$_{4A}$ receptor allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a 5-HT$_{4A}$ receptor and labelled with a detectable marker; e.) detecting labelled bands which have hybridized to the DNA encoding a 5-HT$_{4A}$ receptor labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

BRIEF DESCRIPTION OF FIGURES

FIG. 1: Nucleotide and corresponding amino acid sequence of the S10-87 cDNA clone. (SEQ ID NOS: 1 and 2) Only partial 5' and 3' untranslated sequences are shown.

FIG. 2: Nucleotide and corresponding amino acid sequence of the S10-95 cDNA clone. (SEQ ID NOS: 3 and 4) Only partial 5' and 3' untranslated sequences are shown.

FIG. 3: Comparison of amino acid sequences between clones S10-87 (SEQ ID NO: 2) (top row) and S10-95 (SEQ ID NO: 4) (bottom row). The overall homology is 96.7%.

Figure 4B:
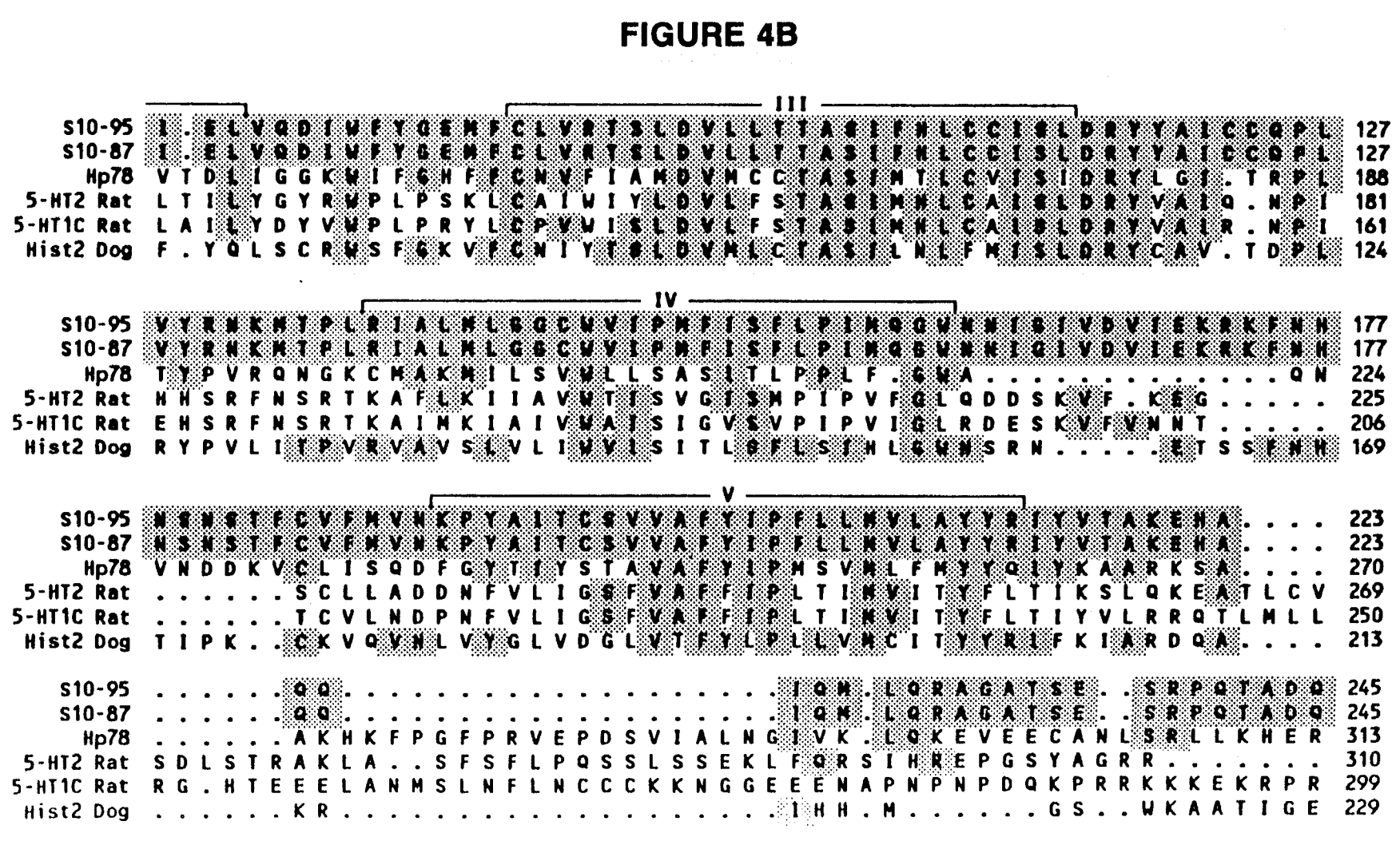
Figure 4C:
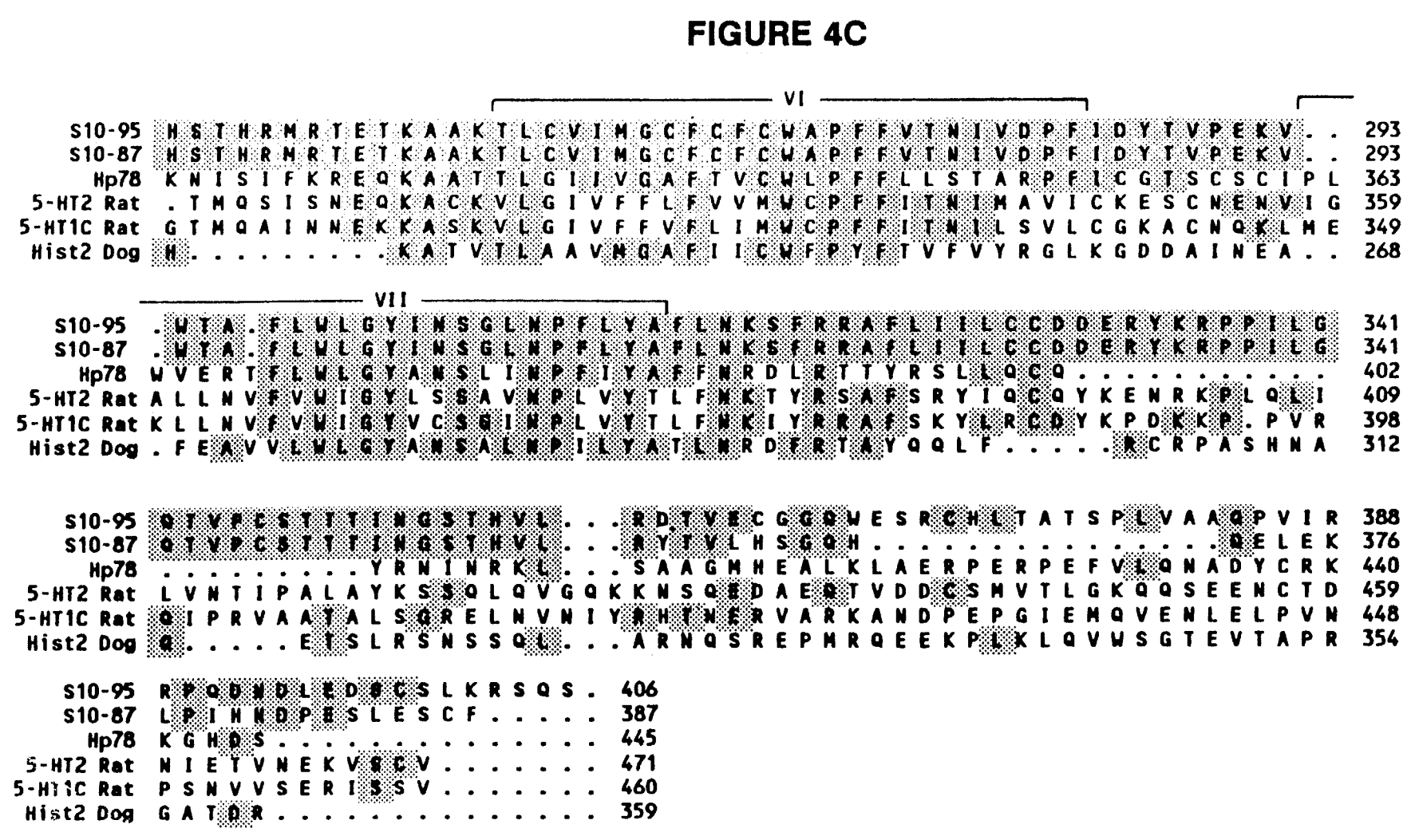

FIG. 4: Comparison of the rat S10 receptor deduced amino acid sequences with those of other serotonin receptors and with the canine histamine H2 receptor. Solid bars, the seven putative membrane-spanning domains (TM I–VII). Shading, homologies between the S10 receptors (SEQ ID NOS: 2 and 4) and other receptors: 5-HT1C (Seq. I.D. No. 9), Hist2 (Seq. I.D. No. 10), 5-HT2 (Seq. I.D. No. 11), Hp78, 5-HT4B or hp78a (Seq. I.D. No. 12). Hp78, 5-HT4B or hp78a receptor (U.S. Ser. No., 971,960, filed, Nov. 3, 1992, copending).

FIG. 5: Nucleotide and amino acid sequences of the human S10 PCR clone. (SEQ ID NOS: 5 and 6) The numbering is given according to the rat S10-95 clone.

FIG. 6: Comparison of nucleotide sequences between the human PCR S10 clone and the rat S10 cDNA clone. Top row: human sequence (SEQ ID NO: 5), the numbering is given according to the rat S10 nucleotide sequence. The bottom row outlines differences in the rat sequence (overall homology: 90.7%).

FIG. 7: Comparison of deduced amino acid sequences between the Human S10 PCR clone and the rat S10 cDNA clone. Top row: human S10 sequence (SEQ ID NO: 6), the numbering is given according to the rat S10 amino acid sequence. The bottom row outlines differences in the rat sequence (overall homology: 92.3 %).

DETAILED DESCRIPTION OF THE INVENTION

Figure 8:
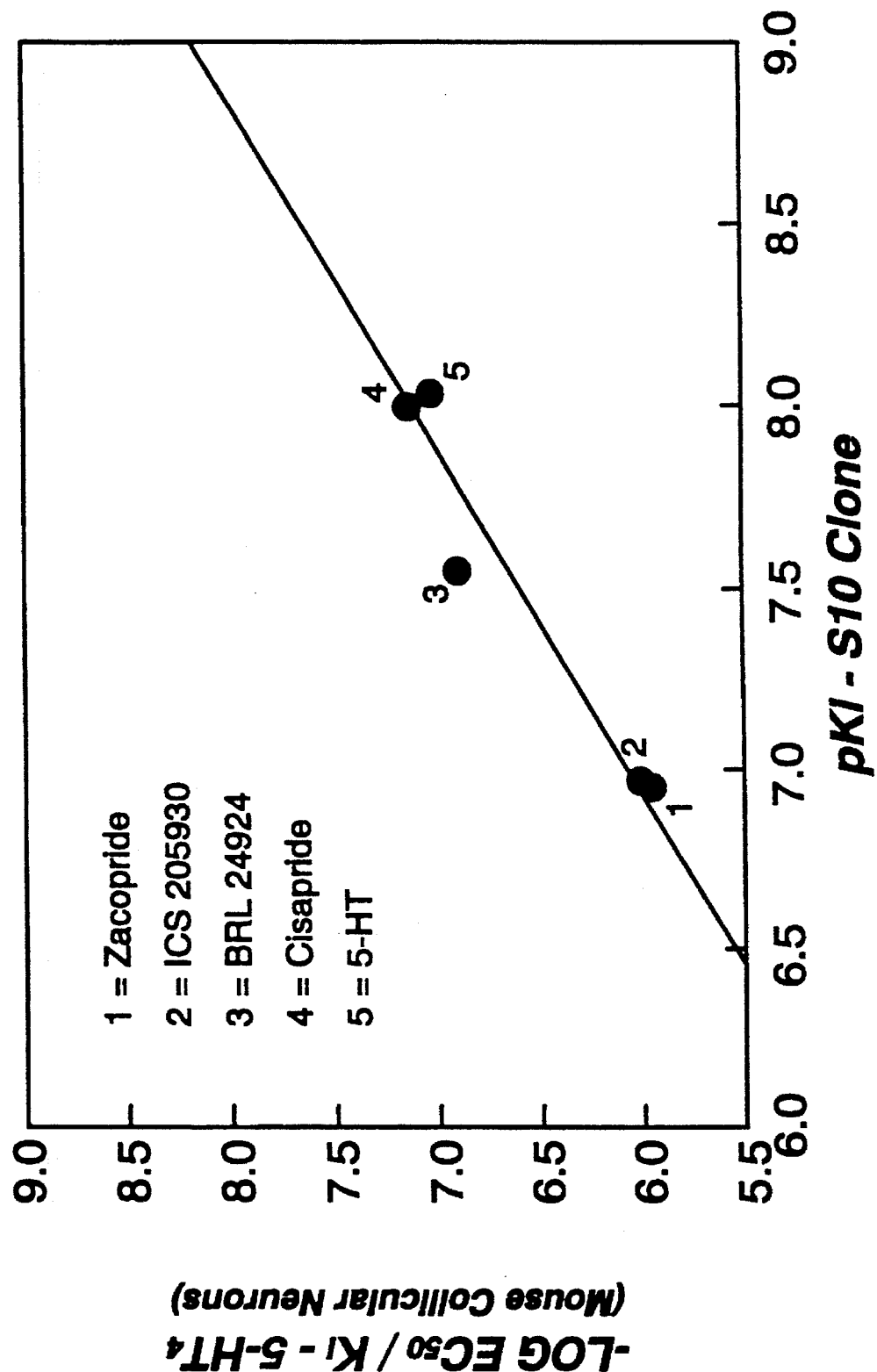
FIG. 8: Comparison of binding affinities of key compounds at the S10 clone with adenylate cyclase functional responses obtained with mouse collicular neurons. A correlation plot was constructed between affinity constants of drugs for the S10 receptor with those obtained at a pharmacologically defined 5-HT$_4$ receptor. Binding values for the correlation were taken from table 1 and were expressed as the negative logarithm. Functional data were taken from Dumuis et al. (1988). The correlation coefficient calculated by linear regression was 0.96 indicating that the rank order of potency for the compounds was similar in both preparations.

This invention provides an isolated nucleic acid molecule encoding a mammalian 5-HT$_{4A}$ receptor. This invention further provides an isolated nucleic acid molecule encoding a human 5-HT$_{4A}$ receptor. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian 5-HT$_{4A}$ receptor or a human 5-HT$_{4A}$ receptor. As used herein, "5-HT$_{4A}$ receptor" means a molecule which, under physiologic conditions, is substantially specific for the neurotransmitter serotonin, is saturable, of high affinity for serotonin and the activation of which is coupled to the activation of adenylate cyclase and the "5-HT$_{4A}$ receptor" is also sensitive to benzamide derivatives which act as agonists and partial agonists at this receptor subtype. One embodiment of this invention is an isolated nucleic acid molecule encoding a mammalian 5-HT$_{4A}$ receptor. Such a molecule may have coding sequences substantially the same as the coding sequences shown in FIGS. 1 and 2 and 5 (SEQ ID NOs. 1, 3 and 5). A preferred embodiment is an isolated nucleic acid molecule encoding a human 5-HT$_{4A}$ receptor. Such a molecule may have a coding sequence substantially the same as the coding sequence shown in FIG. 5 (SEQ ID NO. 5). The DNA molecules of FIGS. 1, 2 and 5 (Seq ID NOs. 1, 3 and 5) encode the sequence of mammalian 5-HT$_{4A}$ receptors. The DNA molecule of FIG. 5 (Seq ID No. 5) encodes a human 5-HT$_{4A}$ receptor. This invention further provides isolated DNA molecules encoding mammalian 5-HT$_{4A}$ receptors having the sequence H$_2$N—Y—X—COOH wherein Y is the amino acid sequence beginning at amino acid 1 and ending at amino acid 359 of FIG. 1 (SEQ ID NOs. 1 and 2) and wherein X is an amino acid sequence encoding the carboxy terminal region of the receptor. The nucleic acid molecules of FIGS. 1 and 2 (SEQ ID NOs 1–4) encode 5-HT$_{4A}$ receptors having an identical sequence Y and differing only in their carboxy terminal region X beginning at amino acid 360. One means of isolating a nucleic acid molecule encoding a mammalian 5-HT$_{4A}$ receptor is to probe a mammalian genomic library with a natural or artificially designed DNA probe, using methods well known in the art. In the preferred embodiment of this invention, the mammalian 5-HT$_{4A}$ receptor is a human protein and the nucleic acid molecule encoding the human 5-HT$_{4A}$ receptor is isolated from human cDNA. Degenerate oligonucleotide primers derived from transmembrane (TM) domains of 5-HT$_{1A}$, 5-HT$_{1C}$, 5-HT$_2$ and 5-HT$_{1D\alpha/\beta}$ receptors are useful for identifying cDNA containing a nucleic acid molecule encoding a 5-HT$_{4A}$ receptor, obtaining a probe specific to a mammalian 5-HT$_{4A}$ receptor and for isolating a nucleic acid molecule encoding a mammalian 5-HT$_{4A}$ receptor.

DNA and cDNA molecules which encode a mammalian 5-HT$_{4A}$ receptor are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has a nucleic acid sequence which differs from the sequence of a nucleic acid molecule encoding a 5-HT$_{4A}$ receptor at one or more nucleotides and which does not encode a protein having 5HT$_{4A}$ receptor activity. As used herein, "5-HT$_{4A}$ receptor activity" means the capability of receptor to specifically bind the neurotransmitter, serotonin under physiological conditions and the capability of the receptor to activate adenylate cyclase when the receptor is coupled to adenylate cyclase. An example of a isolated nucleic acid molecule provided by this invention is a nucleic acid molecule which has an in-frame stop codon inserted into the coding sequence such that the transcribed RNA is not translated into protein.

This invention further provides a cDNA molecule encoding a mammalian 5-HT$_{4A}$ receptor, wherein the cDNA molecule has a coding sequence substantially the same as the coding sequence shown in FIGS. 1, 2 and 5 (Seq ID NOs. 1, 3 and 5). This invention provides a cDNA molecule encoding a human 5-HT$_{4A}$ receptor, wherein the cDNA molecule has a coding sequence substantially the same as the coding sequence shown in FIG. 5 (SEQ ID NO. 5). These molecules and their equivalents were obtained by the means described above.

This invention also provides an isolated protein which is a mammalian 5-HT$_{4A}$ receptor. In a preferred embodiment of this invention, the protein is a human 5-HT$_{4A}$ receptor protein having an amino acid sequence substantially similar to the amino acid sequence shown in FIGS. 1, 2 and 5 (SEQ ID Nos. 1–6). In another embodiment of this invention, the protein is a murine 5-HT$_{4A}$ receptor protein having an amino acid sequence substantially similar to the amino acid sequence shown in FIGS. 1, 2 and 5 (SEQ ID NOs. 1–6). As used herein, the term "isolated protein" is intended to encompass a protein molecule free of other cellular components. One means for obtaining an isolated mammalian 5-HT$_{4A}$ receptor protein is to express DNA encoding the 5-HT$_{4A}$ receptor in a suitable host, such as a bacterial, yeast, or mammalian cell, using methods well known to those skilled in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising DNA, RNA, or cDNA, encoding a mammalian 5-HT$_{4A}$ receptor. This invention further provides a vector comprising DNA, RNA, or cDNA, encoding a human 5-HT$_{4A}$ receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising DNA having a coding sequence substantially the same as the coding sequence shown in FIGS. 1, 2 and 5 (SEQ ID NOs. 1, 3 and 5) and designated pcEXV-S10-87 (ATCC Accession No. 75390), pcEXV-S10-95 (ATCC Accession No. 75391) and pBLuescript-hS10 (ATCC No. 75392), respectively.

Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA or cDNA encoding a mammalian 5-HT$_{4A}$ receptor and vectors comprising a DNA or cDNA encoding a human 5-HT$_{4A}$ receptor, adapted for expression in a bacterial cell, a yeast cell, or a mammalian cell which additionally comprise the regulatory elements necessary for expression of the DNA or cDNA encoding a mammalian 5-HT$_{4A}$ receptor or the DNA or cDNA encoding a human 5-HT$_{4A}$ receptor in the bacterial, yeast, or mammalian cells so located relative to the DNA or cDNA as to permit expression thereof. DNA or cDNA having coding sequence substantially the same as the coding sequence shown in FIGS. 1 and 2 (SEQ ID NOs. 1 and 3) may be usefully inserted into these vectors to express a mantmalian 5-HT$_{4A}$ receptor. DNA or cDNA having a coding sequence substantially the same as the coding sequence shown in FIG. 5 (SEQ ID NO. 5) may be usefully inserted into these vectors to express the human 5-HT$_{4A}$ receptor. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express receptors. Certain uses for such cells are described in more detail below.

In one embodiment of this invention a plasmid is adapted for expression in a bacterial, yeast, or, in particular, a mammalian cell wherein the plasmid comprises DNA or cDNA encoding a mammalian 5-HT$_{4A}$ receptor or DNA or cDNA encoding a human 5-HT$_{4A}$ receptor and the regulatory elements necessary for expression of the DNA in the bacterial, yeast, or mammalian cell so located relative to the DNA or cDNA encoding a mammalian 5-HT$_{4A}$ receptor or to the DNA or cDNA encoding a human 5-HT$_{4A}$ receptor as to permit expression thereof. Suitable plasmids may include, but are not limited to plasmids adapted for expression in a mammalian cell, e.g., EVJB, EXV-3. An example of such a plasmid adapted for expression in a mammalian cell is a plasmid comprising cDNA having coding sequences substantially the same as the coding sequence shown in FIGS. 1, 2 and 5 (SEQ ID NOs. 1, 3 and 5) and the regulatory elements necessary for expression of the DNA in the mammalian cell. These plasmids have been designated pcEXV-S10-87 deposited under ATCC Accession No. 75390, pcEXV-S10-95 deposited under ATCC Accession No. 75391, and pBluescript-hS10, deposited under ATCC Accession No. 75392. Those skilled in the art will readily appreciate that numerous plasmids adapted for expression in a mammalian cell which comprise DNA encoding a mammalian or human 5-HT$_{4A}$ receptor and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

Deposit discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA or cDNA molecule encoding a mammalian 5-HT$_{4A}$ receptor, such as a mammalian cell comprising a plasmid adapted for expression in a mammalian cell, said plasmid further comprises DNA or cDNA encoding a mammalian 5-HT$_{4A}$ receptor and the regulatory elements necessary for expression of the DNA or cDNA in the mammalian cell so located relative to the DNA or cDNA encoding a mammalian 5-HT$_{4A}$ receptor as to permit expression thereof. This invention provides a mammalian cell comprising a DNA or cDNA molecule encoding a human 5-HT$_{4A}$ receptor, such as a mammalian cell comprising a plasmid adapted for expression in a mammalian cell, said plasmid further comprises a DNA or cDNA molecule encoding a human 5-HT$_{4A}$ receptor and the regulatory elements necessary for expression of the DNA or cDNA in the mammalian cell so located relative to the DNA or cDNA encoding a human 5-HT$_{4A}$ receptor as to permit expression thereof. Numerous mammalian cells may be used as hosts, including, but not limited to, the mouse fibroblast cell NIH3T3, CHO cells, HeLa cells, LM (tk−) cells, Cos-7 cells, etc. Expression plasmids such as that described supra may be used to transfect mammalian cells by methods well known in the art such as calcium phosphate precipitation, or DNA or cDNA encoding a human or mammalian 5-HT$_{4A}$ receptor may be otherwise introduced into mammalian cells, e.g., by microinjection, to obtain mammalian cells which comprise DNA, e.g., cDNA or a plasmid, encoding a human or mammalian 5-HT$_{4A}$ receptor.

This invention provides a nucleic acid probe comprising a nucleic acid molecule of at least 15 nucleotides capable of specifically hybridizing with a sequence included within the sequence of a nucleic acid molecule encoding a human 5-$HT_{4A}$ receptor, for example with a coding sequence included within the sequences shown in FIG. 5 (SEQ ID NO. 5). This invention further provides a nucleic acid probe comprising a nucleic acid molecule of at least 15 nucleotides capable of specifically hybridizing with a sequence included within the sequence of a nucleic acid molecule encoding a mammalian 5-$HT_{4A}$ receptor, for example with a coding sequence included within the sequences shown in FIG. 1 and FIG. 2 (SEQ ID NOs. 1 and 3) As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a human 5-$HT_{4A}$ receptor is useful as a diagnostic test for any disease process in which levels of expression of the 5-$HT_{4A}$ receptor are altered. DNA probe molecules are produced by insertion of a DNA molecule which encodes a 5-$HT_{4A}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecules is shown in FIGS. 1, 2 and 5 (SEQ ID NOS. 1, 3, and 5)> The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encode a mammalian 5-$HT_{4A}$ receptor or complementary to the sequence of a DNA molecule which encodes a human 5-$HT_{4A}$ receptor are useful as probes for these genes, for their associated mRNA, or for the isolation of related genes by homology screening of genomic or cDNA libraries, or by the use of amplification techniques such as the polymerase chain reaction.

This invention also provides a method of detecting expression of a human 5-$HT_{4A}$ receptor on the surface of a cell by detecting the presence of mRNA coding for a 5-$HT_{4A}$ receptor. This invention further provides a method of detecting expression of a mammalian 5-$HT_{4A}$ receptor on the surface of the cell by detecting the presence of mRNA coding for a mammalian 5-$HT_{4A}$ receptor. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis et al., 1982). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a human 5-$HT_{4A}$ receptor so as to prevent translation of the human 5-$HT_{4A}$ receptor. The antisense oligonucleotide may have a sequence capable of binding specifically with any sequences of the cDNA molecule whose sequence is shown in FIG. 5 (SEQ ID NO. 5). This invention also provides an antisense oligonucleotide having a sequence capable of binding specifically with any sequences of an mRNA molecule which encodes a mammalian 5-$HT_{4A}$ receptor so as to prevent translation of the mammalian 5-$HT_{4A}$ receptor. The antisense oligonucleotide may have a sequence capable of binding specifically with any sequences of the cDNA molecule whose sequence is shown in FIGS. 1 and 2 (SEQ ID NOs. 1 and 3). As used herein, the phrase "binding specifically" means the ability of an antisense oligonucleotide to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a human 5-$HT_{4A}$ receptor by passing through a cell membrane and binding specifically with mRNA encoding the 5-$HT_{4A}$ receptor in the cell so as to prevent its translation and a pharmaceutically acceptable hydrophobic carrier capable of passing through a cell membrane. This invention further provides a pharmaceutical composition comprising an effective amount of the oligonucleotide described above effective to reduce expression of a mammalian 5-$HT_{4A}$ receptor by passing through a cell membrane and binding specifically with mRNA encoding a mammalian 5-$HT_{4A}$ receptor in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having a coding sequence substantially the same as the coding sequences shown in FIG. 5 (SEQ ID No. 5) may be used as the oligonucleotides of the pharmaceutical composition.

This invention also provides a pharmaceutical composition comprising an effective amount of the oligonucleotide described above effective to reduce expression of a mammalian 5-$HT_{4A}$ receptor by passing through a cell membrane and binding specifically with mRNA encoding the 5-$HT_{4A}$ receptor in the cell so as to prevent its translation and a pharmaceutically acceptable hydrophobic carrier capable of passing through a cell membrane. DNA molecules having a coding sequence substantially the same as the coding sequences shown in FIGS. 1 and 2 (SEQ ID NOs. 1 and 3) may be used as the oligonucleotides of the pharmaceutical composition.

This invention provides a method of treating abnormalities which are alleviated by reduction of expression of 5-HT$_{4A}$ receptor. This method comprises administering to a subject an effective amount of the pharmaceutical composition described above effective to reduce expression of the 5-HT$_{4A}$ receptor by the subject. This invention further provides a method of treating an abnormal condition related to 5-HT$_{4A}$ receptor activity which comprises administering to a subject an amount of the pharmaceutical composition described above effective to reduce expression of the 5-HT$_{4A}$ receptor by the subject. Examples of such abnormal conditions are irritable bowel disease, postoperative ileus, diabetic gastroparesis, emesis, achalasia, hiatal hernia, esophageal spasm and other diseases of the gastrointestinal tract, as well as in cardiac, urinary, and endocrine function.

Antisense oligonucleotide drugs inhibit translation of mRNA encoding 5-HT$_{4A}$ receptor. Synthetic antisense oligonucleotides, or other antisense chemical structures are designed to bind to mRNA encoding the 5-HT$_{4A}$ receptor and inhibit translation of mRNA and are useful as drugs to inhibit expression of 5-HT$_{4A}$ receptor genes in patients. This invention provides a means to therapeutically alter levels of expression of a human or mammalian 5-HT$_{4A}$ receptor by the use of a synthetic antisense oligonucleotide drug (SAOD) which inhibits translation of mRNA encoding the 5-HT$_{4A}$ receptor. Synthetic antisense oligonucleotides, or other antisense chemical structures designed to recognize and selectively bind to mRNA, are constructed to be complementary to portions of the nucleotide sequence shown in FIG. 1, 2 and 5 (SEQ ID NOs. 1, 3 and 5) of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to transporter found only in a certain cell type, as discussed above. The SAOD is also designed to recognize and selectively bind to the target mRNA sequence, which may correspond to a sequence contained within the sequence shown in FIG. 1, 2 and 5 (SEQ ID NOs. 1, 3, and 5) by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen, J. S., 1989; Weintraub, H. M., 1990). In addition, coupling of ribozymes to antisense oligonucleotides is a promising strategy for inactivating target mRNA (N. Sarver et al., 1990). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce 5-HT$_{4A}$ receptor expression in particular target cells of a patient, in any clinical condition which may benefit from reduced expression of 5-HT$_{4A}$ receptor.

This invention provides an antibody directed to the human 5-HT$_{4A}$ receptor. This invention also provides an antibody directed to the mammalian 5-HT$_{4A}$ receptor. This antibody may comprise, for example, a monoclonal antibody directed to an epitope of a human 5-HT$_{4A}$ receptor present on the surface of a cell, the epitope having an amino acid sequence substantially the same as an amino acid sequence for a cell surface epitope of the human 5-HT$_{4A}$ receptor included in the amino acid sequence shown in FIG. 5. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 5 will bind to a surface epitope of a 5-HT$_{4A}$ receptor as described. Antibodies directed to a human or mammalian 5-HT$_{4A}$ receptor may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or LM (tk−) cells may be used as immunogens to raise such an antibody. Alternatively, synthetic peptides may be prepared using commercially available machines and the amino acid sequence shown in FIGS. 1, 2, and 5 (SEQ ID NOs. 1–6). As a still further alternative, DNA, such as a cDNA or a fragment thereof, may be cloned and expressed and the resulting polypeptide recovered and used as an immunogen. These antibodies are useful to detect the presence of 5-HT$_{4A}$ receptor encoded by the isolated DNA, or to inhibit the function of the 5-HT$_{4A}$ receptor in living animals, in humans, or in biological tissues or fluids isolated from animals or humans.

This invention also provides a pharmaceutical composition which comprises an effective amount of an antibody directed to an epitope of the human 5-HT$_{4A}$ receptor, effective to block binding of naturally occurring substrates to the 5-HT$_{4A}$ receptor, and a pharmaceutically acceptable carrier. A monoclonal antibody directed to an epitope of a human 5-HT$_{4A}$ receptor present on the surface of a cell which has an amino acid sequence substantially the same as an amino acid sequence for a cell surface epitope of the human 5-HT$_{4A}$ receptor included in the amino acid sequence shown in FIG. 5 (SEQ ID NOs. 5 and 6) is useful for this purpose.

This invention also provides a pharmaceutical composition which comprises an effective amount of an antibody directed to an epitope of a mammalian 5-HT$_{4A}$ receptor, effective to block binding of naturally occurring substrates to the 5-HT$_{4A}$ receptor, and a pharmaceutically acceptable carrier. A monoclonal antibody directed to an epitope of a mammalian 5-HT$_{4A}$ receptor present on the surface of a cell which has an amino acid sequence substantially the same as an amino acid sequence for a cell surface epitope of a mammalian 5-HT$_{4A}$ receptor included in the amino acid sequence shown in FIGS. 1 and 2 (SEQ ID NOs. 1–4) is useful for this purpose. This invention also provides a method of treating abnormalities in a subject which are alleviated by reduction of expression of a human or mammalian 5-HT$_{4A}$ receptor which comprises administering to the subject an effective amount of the pharmaceutical composition described above effective to block binding of naturally occurring substrates to the receptor and thereby alleviate abnormalities resulting from overexpression of a human or mammalian 5-HT$_{4A}$ receptor. Binding of the antibody to the receptor prevents the receptor from functioning, thereby neutralizing the effects of overexpression. The monoclonal antibodies described above are useful for this purpose. This invention additionally provides a method of treating an abnormal condition related to an excess of 5-HT$_{4A}$ receptor activity which comprises administering to a subject an amount of the pharmaceutical composition described above effective to block binding of naturally occurring substrates to the 5-HT$_{4A}$ receptor and thereby alleviate the abnormal condition. Some examples of abnormal conditions associated with excess 5-HT$_{4A}$ receptor activity are irritable bowel disease, postoperative ileus, diabetic gastroparesis, emesis, achalasia, hiatal hernia, esophageal spasm and other diseases of the gastrointestinal tract, as well as in cardiac, urinary, and endocrine function.

This invention provides methods of detecting the presence of a 5-HT$_{4A}$ receptor on the surface of a cell which comprises contacting the cell with an antibody directed to the 5-HT$_{4A}$ receptor, under conditions permitting binding of the antibody to the receptor, detecting the presence of the antibody bound to the cell, and thereby the presence of the 5-HT$_{4A}$ receptor on the surface of the cell. Such methods are useful for determining whether a given cell is defective in expression of 5-HT$_{4A}$ receptors. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human 5-HT$_{4A}$ receptor and a transgenic nonhuman mammal expressing DNA encoding a mammalian 5-HT$_{4A}$ receptor. This invention also provides a transgenic nonhuman mammal expressing DNA encoding a human or mammalian 5-HT$_{4A}$ receptor so mutated as to be incapable of normal receptor activity, and not expressing native 5-HT$_{4A}$ receptor. This invention further provides a transgenic nonhuman mammal whose genome comprises DNA encoding a human 5-HT$_{4A}$ receptor so placed as to be transcribed into antisense mRNA which is complementary to mRNA encoding a human 5-HT$_{4A}$ receptor and which hybridizes to mRNA encoding a 5-HT$_{4A}$ receptor thereby reducing its translation and a transgenic nonhuman mammal whose genome comprises DNA encoding a mammalian 5-HT$_{4A}$ receptor so placed as to be transcribed into antisense mRNA which is complementary to mRNA encoding a mammalian 5-HT$_{4A}$ receptor and which hybridizes to mRNA encoding a mammalian 5-HT$_{4A}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIG. 1, 2 and 5 (SEQ ID NOs. 1, 3, and 5). An example of a transgenic animal is a transgenic mouse. Examples of tissue specificity-determining regions are the metallothionein promotor (Low et al., 1986) and the L7 promotor (Oberdick et al., 1990).

Animal model systems which elucidate the physiological and behavioral roles of mammalian receptors are produced by creating transgenic animals in which the expression of a receptor is either increased or decreased, or the amino acid sequence of the expressed receptor protein is altered, by a variety of techniques. Examples of these techniques include, but are not limited to: 1) Insertion of normal or mutant versions of DNA encoding a human 5-HT$_{4A}$ receptor or homologous animal versions of this gene, by microinjection, retroviral infection or other means well known to those skilled in the art, into appropriate fertilized embryos in order to produce a transgenic animal (Hogan et al., 1986) or, 2) Homologous recombination (Capecchi M. R., 1989; Zimmer A, and Gruss, P., 1989) of mutant or normal, human or animal versions of these genes with the native gene locus in transgenic animals to alter the regulation of expression or the structure of the receptor. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor.

One means available for producing a transgenic animal, with a mouse as an example, is as follows: Female mice are mated, and the resulting fertilized eggs are dissected out of their oviducts. The eggs are stored in an appropriate medium such as M2 medium (Hogan, B. et al. 1986). DNA or cDNA encoding a receptor is purified from a vector (such as plasmids pcEXV-S10-87, pcEXV-S10-95 and pBluescript-hS10 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against the receptors even before such drugs become available. These animal model systems are useful for predicting or evaluating possible therapeutic applications of drugs which activate or inhibit receptors by inducing or inhibiting expression of the native or trans-gene and thus increasing or decreasing expression of normal or mutant receptors in the living animal. Thus, a model system is produced in which the biological activity of drugs directed against the receptors are evaluated before such drugs become available. The transgenic animals which over or under produce the receptor indicate by their physiological state whether over or under production of the receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to the receptor is indicated as worth developing, and if a promising therapeutic application is uncovered by these animal model systems, activation or inhibition of the 5-$HT_{4A}$ receptor is achieved therapeutically either by producing agonist or antagonist drugs directed against the 5-$HT_{4A}$ receptor or by any method which increases or decreases the expression of this receptor in man.

Further provided by this invention is a method of determining the physiological effects of expressing varying levels of human or mammalian 5-$HT_{4A}$ receptors which comprises producing a transgenic nonhuman animal whose levels of human or mammalian 5-$HT_{4A}$ receptor expression are varied by use of an inducible promoter which regulates receptor expression. This invention also provides a method of determining the physiological effects of expressing varying levels of human or mammalian 5-$HT_{4A}$ receptor which comprises producing a panel of transgenic nonhuman animals each expressing a different amount of human or mammalian 5-$HT_{4A}$ receptor. Such animals may be produced by introducing different amounts of DNA encoding a human or mammalian 5-$HT_{4A}$ receptor into the oocytes from which the transgenic animals are developed.

This invention also provides a method for identifying a substance capable of alleviating abnormalities resulting from overexpression of a human or mammalian 5-$HT_{4A}$ receptor comprising administering the substance to a transgenic nonhuman mammal expressing at least one artificially introduced DNA molecule encoding a human or mammalian 5-$HT_{4A}$ receptor and determining whether the substance alleviates the physical and behavioral abnormalities displayed by the transgenic nonhuman mammal as a result of overexpression of a human or mammalian 5-$HT_{4A}$ receptor. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1, 2, and 5 (SEQ ID NOs. 1, 3, and 5).

This invention provides a pharmaceutical composition comprising an amount of the substance described supra effective to alleviate the abnormalities resulting from overexpression of 5-$HT_{4A}$ receptor and a pharmaceutically acceptable carrier.

This invention further provides a method for treating the abnormalities resulting from overexpression of a human or mammalian 5-$HT_{4A}$ receptor which comprises administering to a subject an amount of the pharmaceutical composition described above effective to alleviate the abnormalities resulting from overexpression of a human or mammalian 5-$HT_{4A}$ receptor.

This invention provides a method for identifying a substance capable of alleviating the abnormalities resulting from underexpression of a human or mammalian 5-$HT_{4A}$ receptor comprising administering the substance to the transgenic nonhuman mammal described above which expresses only nonfunctional human or mammalian 5-$HT_{4A}$ receptor and determining whether the substance alleviates the physical and behavioral abnormalities displayed by the transgenic nonhuman mammal as a result of underexpression of a human or mammalian 5-$HT_{4A}$ receptor.

This invention also provides a pharmaceutical composition comprising an amount of a substance effective to alleviate abnormalities resulting from underexpression of a human or mammalian 5-$HT_{4A}$ receptor and a pharmaceutically acceptable carrier.

This invention further provides a method for treating the abnormalities resulting from underexpression of a human or mammalian 5-$HT_{4A}$ receptor which comprises administering to a subject an amount of the pharmaceutical composition described above effective to alleviate the abnormalities resulting from underexpression of a human or mammalian 5-$HT_{4A}$ receptor.

This invention provides a method for diagnosing a predisposition to a disorder associated with the expression of a human or mammalian 5-$HT_{4A}$ receptor allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human or mammalian 5-$HT_{4A}$ receptor and labelled with a detectable marker; e) detecting labelled bands which have hybridized to the DNA encoding a human or mammalian 5-$HT_{4A}$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-$HT_{4A}$ receptor allele or mammalian 5-$HT_{4A}$ receptor allele.

This invention provides a method of preparing the isolated 5-$HT_{4A}$ receptor which comprises inducing cells to express receptor, recovering the receptor from the resulting cells, and purifying the receptor so recovered. An example of a 5-$HT_{4A}$ receptor is an isolated protein having substantially the same amino acid sequence as the amino acid sequence shown in FIG. 5. For example, cells can be induced to express receptors by exposure to substances such as hormones. The cells can then be homogenized and the receptor isolated from the homogenate using an affinity column comprising, for example serotonin or another substance which is known to bind to the 5-$HT_{4A}$ receptor. The resulting fractions can then be purified by contacting them with an ion exchange column, and determining which fraction contains 5-HT$_{4A}$ receptor activity or binds anti-receptor antibodies.

This invention provides a method of preparing an isolated human 5-HT$_{4A}$ receptor which comprises inserting nucleic acid encoding the human 5-HT$_{4A}$ receptor in a suitable vector, inserting the resulting vector in a suitable host cell, recovering the receptor produced by the resulting cell, and purifying the receptor so recovered. An example of an isolated human 5-HT$_{4A}$ receptor is an isolated protein having substantially the same amino acid sequence as the amino acid sequence shown in FIG. 5 (SEQ ID NOs. 5 and 6). This invention provides a method of preparing an isolated mammalian 5-HT$_{4A}$ receptor which comprises inserting nucleic acid encoding the mammalian 5-HT$_{4A}$ receptor in a suitable vector, inserting the resulting vector in a suitable host cell, recovering the receptor produced by the resulting cell, and purifying the receptor so recovered. An example of an isolated mammalian 5-HT$_{4A}$ receptor is an isolated protein having substantially the same amino acid sequence as the amino acid sequence shown in FIGS. 1 and 2 (SEQ ID NOs. 1–2 and Seq I.D. Nos. 3–4, respectively). These methods for preparing 5-HT$_{4A}$ receptor uses recombinant DNA technology methods well known in the art. For example, isolated nucleic acid encoding 5-HT$_{4A}$ receptor is inserted in a suitable vector, such as an expression vector. A suitable host cell, such as a bacterial cell, or a eukaryotic cell such as a yeast cell, is transfected with the vector. 5-HT$_{4A}$ receptor is isolated from the culture medium by affinity purification or by chromotography or other methods well known in the art.

This invention provides a method for determining whether a compound not known to be capable of specifically binding to a human 5-HT$_{4A}$ receptor can specifically bind to the human 5-HT$_{4A}$ receptor, which comprises contacting a mammalian cell comprising a plasmid adapted for expression in a mammalian cell which plasmid further comprises a DNA which expresses a human 5-HT$_{4A}$ receptor on the cell's surface with the compound under conditions permitting binding of ligands known to bind to a human 5HT$_{4A}$ receptor, detecting the presence of any compound bound to the human 5-HT$_{4A}$ receptor, the presence of bound compound indicating that the compound is capable of specifically binding to the human 5-HT$_{4A}$ receptor.

This invention provides a method for determining whether a compound not known to be capable of specifically binding to a mammalian 5-HT$_{4A}$ receptor can specifically bind to the mammalian 5-HT$_{4A}$ receptor, which comprises contacting a mammalian cell comprising a plasmid adapted for expression in a mammalian cell which plasmid further comprises a DNA which expresses a mammalian 5-HT$_{4A}$ receptor on the cell's surface with the compound under conditions permitting binding of ligands known to bind to a mammalian 5-HT$_{4A}$ receptor, detecting the presence of any compound bound to the mammalian 5-HT$_{4A}$ receptor, the presence of bound compound indicating that the compound is capable of specifically binding to the mammalian 5-HT$_{4A}$ receptor.

This invention provides a method for identifying a compound which is not known to be capable of binding to a human 5-HT$_{4A}$ receptor can functionally activate the human 5-HT$_{4A}$ receptor on the surface of a mammalian cell or prevent a ligand which does so, which comprises contacting the mammalian cell which cell comprises a plasmid adapted for expression in the mammalian cell such plasmid further comprising DNA which expresses the human 5-HT$_{4A}$ receptor on the surface of the mammalian cell with the compound, determining whether the compound activates the human 5-HT$_{4A}$ receptor or prevents a ligand which does so, and thereby identifying the compound as a compound which is binds to and functionally activates the human 5-HT$_{4A}$ receptor or prevents the functional activation of the human 5-HT$_{4A}$ receptor by a ligand which does so. The DNA in the cell may have a coding sequence substantially the same as the coding sequence shown in FIG. 5 ( SEQ ID No. 5).

This invention provides a method for identifying a compound which is not known to be capable of binding to a mammalian 5-HT$_{4A}$ receptor can functionally activate the mammalian 5-HT$_{4A}$ receptor on the surface of a mammalian cell or prevent a ligand which does so, which comprises contacting the mammalian cell which cell comprises a plasmid adapted for expression in the mammalian cell such plasmid further comprising DNA which expresses the mammalian 5-HT$_{4A}$ receptor on the surface of the mammalian cell with the compound, determining whether the compound activates the mammalian 5-HT$_{4A}$ receptor or prevents a ligand which does so, and thereby identifying the compound as a compound which is binds to and functionally activates the mammalian 5-HT$_{4A}$ receptor or prevents the functional activation of the mammalian 5-HT$_{4A}$ receptor by a ligand which does so. The DNA in the cell may have a coding sequence substantially the same as the coding sequence shown in FIGS. 1 and 2 (SEQ ID NOs. 1 and 3).

The activation or blockade of the functional response is detected by means of a bioassay from the mammalian cell such as a second messenger response, and thereby determining whether the compound activates or prevents the activation of the 5-HT$_{4A}$ receptor functional output. Preferably, the mammalian cell is nonneuronal in origin. An example of a nonneuronal mammalian cell is an LM (tk–) cell. Another example of a non-neuronal mammalian cell to be used for functional assays is a murine fibroblast cell line, specifically the NIH3T3 cell. The preferred method for determining whether a compound is capable of binding to the 5-HT$_{4A}$ receptor comprises contacting a transfected nonneuronal mammalian cell (i.e. a cell that does not naturally express any type of 5-HT or G-protein coupled receptor, thus will only express such a receptor if it is transfected into the cell) expressing a 5-HT$_{4A}$ receptor on its surface, or contacting a membrane preparation derived from such a transfected cell, with the compound under conditions which are known to prevail, and thus to be associated with, in vivo binding of ligands to a 5-HT$_{4A}$ receptor, detecting the presence of any of the compound being tested bound to the 5-HT$_{4A}$ receptor on the surface of the cell, and thereby determining whether the compound binds to, and activates or prevents the activation of the 5-HT$_{4A}$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from preexisting cell lines, or can be generated by inserting appropriate components of second messenger systems into existing cell lines. Such a transfection system provides a complete response system for investigation or assay of the activity of human 5-HT$_{4A}$ receptor with compounds as described above.

Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{4A}$ receptor. The transfection system is also useful for determining the affinity and efficacy of known drugs at human 5-HT$_{4A}$ receptor sites.

This invention also provides a method of screening compounds to identify drugs which interact with, and specifically bind to, a human 5-HT$_{4A}$ receptor on the surface of a cell, which comprises contacting a mammalian cell which comprises a plasmid adapted for expression in a mammalian cell which plasmid further comprises DNA which expresses a human 5-HT$_{4A}$ receptor on the cell's surface with a plurality of compounds, determining those compounds which bind to the human 5-HT$_{4A}$ receptor expressed on the cell surface of the mammalian cell, and thereby identifying compounds which interact with, and specifically bind to, the human 5-HT$_{4A}$ receptor. The DNA in the cell may have a coding sequence substantially the same as the coding sequence shown in FIG. 5 (SEQ ID NO. 5). This invention also provides a method of screening compounds to identify drugs which interact with, and specifically bind to, a mammalian 5-HT$_{4A}$ receptor on the surface of a cell, which comprises contacting a mammalian cell which comprises a plasmid adapted for expression in a mammalian cell which plasmid further comprises DNA which expresses a mammalian 5-HT$_{4A}$ receptor on the cell's surface with a plurality of compounds, determining those compounds which bind to the mammalian 5-HT$_{4A}$ receptor expressed on the cell surface of the mammalian cell, and thereby identifying compounds which interact with, and specifically bind to, the mammalian 5-HT$_{4A}$ receptor. The DNA in the cell may have a coding sequence substantially the same as the coding sequence shown in FIGS. 1 and 3 (SEQ ID NOs. 1 and 2). Various methods of detection may be employed. The compounds may be "labeled" by association with a detectable marker substance (e.g., radiolabel or a non-isotopic label such as biotin). Preferably, the mammalian cell is nonneuronal in origin. An example of a nonneuronal mammalian cell is a Cos-7 cell. Drug candidates are identified by choosing chemical compounds which bind with high affinity to the expressed 5-HT$_{4A}$ receptor protein in transfected cells, using radioligand binding methods well known in the art, examples of which are shown in the binding assays described herein. Drug candidates are also screened for selectivity by identifying compounds which bind with high affinity to one particular receptor but do not bind with high affinity to any other receptor subtypes or to any other known receptor. Because selective, high affinity compounds interact primarily with the target 5-HT$_{4A}$ receptor site after administration to the patient, the chances of producing a drug with unwanted side effects are minimized by this approach.

This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bioavailable following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bioavailable, in an appropriate solid or solution formulation, to gain the desired therapeutic benefit.

Applicants have identified a novel 5-HT receptor subtype protein, designated 5-HT$_{4A}$ and have described methods for the identification of pharmacological compounds for therapeutic treatments. Pharmacological compounds which are directed against specific receptor subtypes provide effective new therapies with minimal side effects.

Elucidation of the molecular structures of the neuronal serotonin receptors is an important step in the understanding of serotonergic neurotransmission. This disclosure reports the isolation and amino acid sequence of a novel cDNA which encodes a human 5-HT$_{4A}$ receptor. This disclosure reports the isolation, amino acid sequence, and functional expression of a two novel cDNAs which encode mammalian 5-HT$_{4A}$ receptors. The identification of 5-HT receptor subtypes play a pivotal role in elucidating the molecular mechanisms underlying serotonergic transmission, and should also aid in the development of novel therapeutic agents.

A complementary DNA clone (designated pBluescript-hS10) encoding a serotonin receptor subtype, 5HT$_{4A}$, has been isolated from human brain, human heart and human retina. Additionally, two complementary DNA clones encoding the serotonin 5HT$_{4A}$ receptor subtype have been isolated from mammalian brain and their functional properties have been examined in mammalian cells. Analysis of 5-HT$_{4A}$ structure and function provides a model for the development of drugs useful for the treatment of gastrointestinal conditions including irritable bowel disease, postoperative ileus, diabetic gastroparesis, emesis, achalasia, hiatal hernia, and esophageal spasm. In addition, 5-HT$_4$ receptors have been described functionally in the heart (Kaumann, 1992), adrenal (Lefebvre et al., 1992), and bladder (Corsi et al., 1991) indicating possible roles in cardiac rate and force of contraction, endocrine control of cortisol secretion, and urinary incontinence or spasticity. 5-HT$_4$ receptors have also been described in the brain, particularly in areas such as the hippocampus, in which we have localized the gene encoding 5-HT$_4$ receptors (S10-95), indicating a potential role in cognitive enhancement (Bockaert et al., 1992).

This invention identifies a mammalian serotonin receptor, its amino acid sequence, and its mammalian gene, the activation of which is coupled to activation of adenylate cyclase. The information and experimental tools provided by this discovery are useful to generate new therapeutic agents, and new therapeutic or diagnostic assays for this receptor protein, its associated mRNA molecule or its associated genomic DNA. The information and experimental tools provided by this discovery will be useful to generate new therapeutic agents, and new therapeutic or diagnostic assays for this new serotonin receptor subtype, its associated mRNA molecule, or its associated genomic DNA.

Specifically, this invention relates to the isolation of human cDNA clone and mammalian cDNA clones encoding a new serotonin receptor, designated 5-HT$_{4A}$. In addition, the mammalian 5-HT$_{4A}$ receptors have been expressed in COS7 cells by transfecting the cells with the plasmids pcEXV-S10-87 and pcEXV-S10-95. The pharmacological binding properties of the encoded 5-HT$_{4A}$ receptor have been determined, and the binding properties classify this receptor as a novel serotonin receptor. Mammalian cell lines expressing the mammalian 5-HT$_{4A}$ receptor on the cell surface have been constructed, thus establishing the first well-defined, cultured cell lines with which to study the novel 5-HT$_{4A}$ receptor.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Methods and Materials

PCR Amplification: The third (III) and fifth (V) transmembrane (TM) domains of the following receptors were aligned and used to synthesize a pair of degenerate primers: 5-HT$_{1A}$, 5-HT$_{1C}$, 5-HT$_2$ and the 5-HT$_{1D\alpha/\beta}$ receptors. Primers 3.17 and 5.5 ([5'-TGGAATTCTG(C/T)G(C/T)IAT(A/C/T) (G/T)CUCTGGA(C/T) (A/C)G(C/G) TA-3'] (SEQ. I.D. NO. 7), [5'-CATIA(G/C/A)I(G/A)IIA(G/A)IGG(T/G/A/)AT(G/A) (T/A)A(G/A) AAIGC-3']) (SEQ. I.D. NO. 8) were used to amplify 5 µg of poly (A+) RNA from rat brain that was reverse transcribed by avian myeloblastosis virus reverse transcriptase (AMV). PCR was performed on single-stranded cDNA under the following conditions: 94° C. for 1 min, 50° C. for 2 min and 72° C. for 3 min for 40 cycles. Following PCR, 90 µl of the reaction was phenol:chloroform extracted and precipitated; 10 µl was visualized using on a gel ethidium bromide staining. After precipitation the sample was treated with T4 DNA polymerase and digested with EcoR1 prior to separation on a 1% agarose gel. The DNA fragments (200 to 400 base pairs) were isolated from the gel, kinased and cloned into pBluescript. Recombinant clones were analyzed by sequencing. One fragment 270 base pairs in length, named S10, was identified. This sequence contained a "TM IV" like domain and represented a potentially new serotonin receptor. The corresponding full length cDNA was isolated from a rat brain cDNA library.

Rat PCR primers (from TM3 to TM7) were used to amplify single-stranded cDNA prepared from human heart, brain and retina, as described above. Those human PCR DNA fragments were subcloned in pBluescript and sequenced.

cDNA Library Construction, Screening and Sequencing: Rat brains were dissected from adult male CD rats (Charles River Laboratories) and total RNA was prepared by the guanidine thiocyanate method (Chirgwin, J. W. et al.; 1979). Poly A$^+$RNA was purified with a Fast track kit (Invitrogen Corp., San Diego, Calif.). Double stranded (DS) cDNA was synthesized from 5 µg of poly A$^+$RNA according to Gubler and Hoffman (Gubler, U. and B. J. Hoffman, 1983). The resulting DS cDNA was ligated to BstxI/EcoRI adaptors (Invitrogen Corp.), the excess of adaptors was removed by chromatography on Sepharose CL 4B (Pharmacia LKB) and the DNA was then size selected on a Gen-Pak Fax HPLC column (Zhao, D. et al., 1992) (Waters, Millipore Corp., Milford, Mass.). High molecular weight fractions were ligated in pCDM8 cut by BstxI (Invitrogen Corp.). The ligated DNA was electroporated in E.Coli MC 1061 (Gene Pulser, Biorad). A total of 20×10$^6$ independent clones with an insert mean size of 1.9 kb could be generated. Before amplification, the library was divided into pools of 2.5×10$^4$ independent clones. After 18 hours amplification, the pools were stored at −85° C. in 20% glycerol.

100 pools of the cDNA library, representing 3.2×10$^6$ primary clones, were screened using exact PCR primers derived from the S10 PCR clone sequence. 1 µl (4×10$^6$ bacteria) of each amplified pool was subjected directly to 40 cycles of PCR and the resulting products analyzed by agarose gel electrophoresis and Southern blotting. Two out of four positive pools were analyzed further and by sib selection and plating out, two individual full length cDNA clones, S10-87 and S10-95, were isolated. DS-DNA was sequenced with a sequanase kit (US Biochemical, Cleveland, Ohio) according to the manufacturer. Nucleotide and peptide sequences analysis were performed with GCG programs.

DNA transfection: The full coding region of S10-87 and S10-95 were subcloned in the correct orientation in the mammalian expression vectors pCDNA1-Amp (Invitrogen Corp.) (CG-5 and CG-6 respectively), and pcEXV-3 (Miller, J. and R. N. Germain, 1986) (CG-7 and CG-8 respectively). For transient expression, Cos-7 cells were transfected by the DEAE-Dextran method, using 1 µg of DNA /10$^6$ cells (Warden, D. and H. V. Thorne, 1968).

Membrane Preparation: Membranes were prepared from transiently transfected COS-7 cells which were grown to 100% confluence. The cells were washed twice with phosphate-buffered saline, scraped from the culture dishes into 5 ml of ice-cold phosphate-buffered saline, and centrifuged at 200× g for 5 min at 4°. The pellet was resuspended in 2.5 ml of ice-cold Tris buffer (20 mM Tris -HCl, pH 7.4 at 23°, 5 mM EDTA), and homogenized by a Wheaton tissue grinder. The lysate was subsequently centrifuged at 200× g for 5 min at 4° to pellet large fragments which were discarded. The supernatant was collected and centrifuged at 40,000× g for 20 min at 4°. The pellet resulting from this centrifugation was washed once in ice-cold Tris wash buffer and finally resuspended in a final buffer containing 50 mM Tris-HCl and 0.5 mM EDTA, pH 7.4 at 23°. Membrane preparations were kept on ice and utilized within two hr for the radioligand binding assays. Protein concentrations were determined by the method of Bradford (1976) using bovine serum albumin as the standard.

Radioligand Binding: [$^3$H]5-HT binding was performed using slight modifications of the 5-HT$_{1D}$ assay conditions reported by Herrick-Davis and Titeler (1989) with the omission of masking ligands. Radioligand binding studies were achieved at 37° C. in a total volume of 250 µl of buffer (50 mM Tris, 10 mM MgCl$_2$, 0.2 mM EDTA, 10 µM pargyline, 0.1% ascorbate, pH 7.4 at 37° C.) in 96 well microtiter plates. Saturation studies were conducted using [$^3$H]5-HT at 10 different concentrations ranging from 1.0 nM to 100 nM. Displacement studies were performed using 10 nM [$^3$H]5-HT. The binding profile of drugs in competition experiments was established using 7 concentrations of compound. Incubation times were 30 min for both saturation and displacement studies. Nonspecific binding was defined in the presence of 10 µM 5-HT. Binding was initiated by the addition of 50 µl membrane homogenates (10–20 µg). The reaction was terminated by rapid filtration through presoaked (0.5% polyethyleneimine) filters using 48R Cell Brandel Harvester (Gaithersburg, Md.). Subsequently, filters were washed for 5 sec with ice cold buffer (50 mM Tris HCL, pH 7.4 at 4° C.), dried and placed into vials containing 2.5 ml of Readi-Safe (Beckman, Fullerton, Calif.), and radioactivity was measured using a Beckman LS 6500C liquid scintillation counter. The efficiency of counting of [$^3$H]5-HT averaged between 45–50%. Binding data were analyzed by computer-assisted nonlinear regression analysis (Accufit and Accucomp, Lundon Software, Chagrin Falls, Ohio). IC$_{50}$ values were converted to K$_i$ values using the Cheng-Prusoff equation (1973).

Measurement of cAMP Formation: The transiently transfected Cos-7 cells were incubated in Dulbecco's modified Eagle's medium, 5 mM theophylline, 10 mM Hepes (4-[2-Hydroxyethyl]-1-piperazineethanesulfonic acid), 10 µM pargyline, and/or appropriate concentrations of antagonists for 20 minutes at 37° C., 5% $CO_2$. Serotonin or other agonists in the presence or absence of forskolin (FSK) (10 µM) were then added at appropriate concentrations and incubated for an additional 10 minutes at 37° C. 5% $CO_2$. The media was aspirated and the reaction stopped by the addition of 100 mM HCl. The plates were stored at 4° C. for 15 minutes, centrifuged for 5 minutes, 500× g to pellet cellular debris, and the supernatant aliquotted and stored at −20° C. prior to assessment of cAMP formation by radioimmunoassay (cAMP Radioimmunoassay kit, Advanced Magnetics, Cambridge, Mass.). Radioactivity was quantitatied using a Packard COBRA Auto Gamma Counter equipped with data reduction software. Functional data was fitted to a four parameter logistic equation to obtain response parameters ($EC_{50}$, $E_{max}$, nH; Inplot, GraphPad, San Diego, Calif.).

Drugs: [$^3$H]5-HT (specific activity=22.7 Ci/mmole) was obtained from New England Nuclear, Boston, Mass. All other chemicals were obtained from commercial sources and were of the highest grade purity available.

Experimental Results

Figures 4A, 4B, 4C:
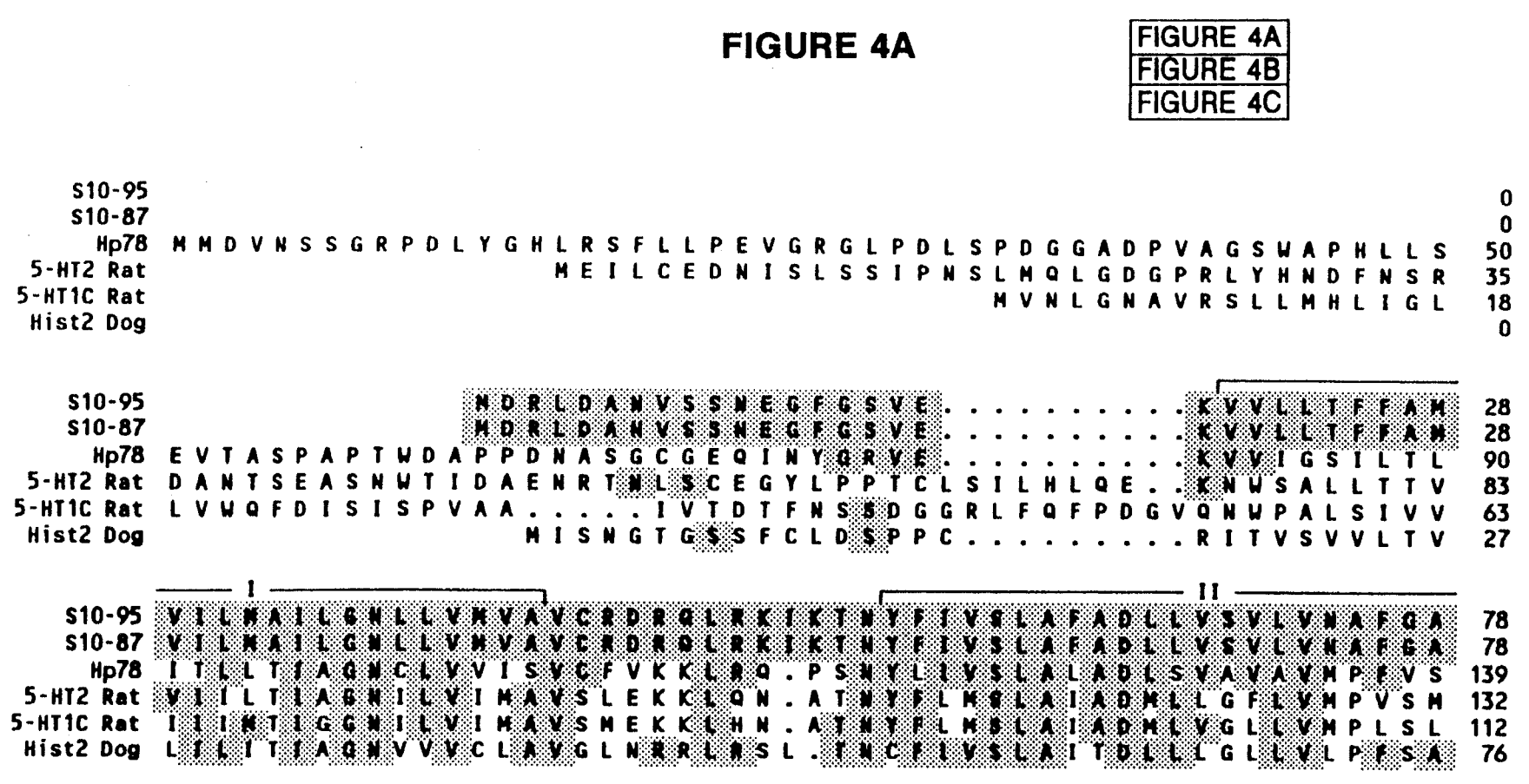

A 270 bp DNA fragment (S10) was identified when rat brain cDNA was used as template in a PCR amplification with two degenerate oligonucleotide primers derived from well conserved regions among several serotonin receptors, in the third and fifth putative transmembrane domains. The peptide sequence corresponding to this S10 PCR clone contained a "transmembrane IV like" domain. Since we used "serotonin receptor specific" PCR primers, this S10 clone represented a potentially new serotonin receptor. The corresponding full length cDNA was isolated from a rat brain cDNA library. Since five amplified commercial phage cDNA libraries turned out to be negative, we split the plasmid cDNA library into small pools of 2.5 to 5×10$^4$ independent clones before amplification to avoid a potential growth bias against the S10 cDNA clone. By direct PCR analysis of bacterial pools, subsequent sib selection and standard filter hybridization, two cDNA clones were identified, S10-87 (5.5 kb) and S10-95 (4.5 kb). The nucleotide and deduced amino acid sequences are shown in FIG. 1 (S10-87) and FIG. 2 (S10-95). Surprisingly the peptide sequences between those two clones are only 96.7% identical, diverging in the second half of the carboxy terminus tails, downstream of position 359 (FIG. 3). In addition, the entire 3' untranslated regions are totally divergent. The longest open reading frame for S10-87 encodes a protein of 387 amino acids and 406 amino acids for S10-95. The hydrophobicity plot displayed seven hydrophobic, putative membrane spanning regions which when compared to other G protein-coupled receptors did not show any significant high homologies, even to other serotonin receptors (Table 1 and FIG. 4). It is interesting to note that the highest homology, overall or restricted to the 7 TM region, is exhibited by the human histamine $H_2$ receptor, which like the 5-$HT_4$ receptor, is coupled to stimulation of cAMP.

Both S10-87 and S10-95 proteins carry 4 potential N-glycosylation sites in positions 7, 180, 316, and 352. They also possess 3 potential phosphorylation sites for protein kinase C in positions 218, 248, 318 and 4 potential phosphorylation sites for casein kinase II in positions 9, 97,218 and 288. A potential palmitoylation site is present in both clones at the cysteine found in position 329. A large number of G protein-coupled receptors carry a cysteine in the same position and O'Dowd et al. have speculated that it plays an important role in the functional coupling of the human $\beta_2$-adrenergic receptor. In addition, clone S10-95 carries one more potential phosphorylation site for protein kinase C at position 400. This additional phosphorylation site could lead to differential functional coupling between the S10-87 and S10-95 receptors.

Since we isolated two different S10 cDNA clones by screening a library made from an entire brain, we checked for differential expression in seven different parts-of the brain by PCR amplification using pairs of primers specific for each clone. The results are summarized in table 2. Clone S10-95 seems to be transcribed everywhere in the rat brain except in cerebellum. Clone S10-87 is only expressed in striatum. It remains to be determined if only one or both receptors are expressed in rat cortex.

The human PCR cDNA fragments (TM-3 to TM-7) are 100% identical between heart, brain and retina. The nucleotide and deduced amino acid sequences are shown in FIG. 5. The human sequence shows 90.7% homology with the rat nucleotide sequence (FIG. 6) and 92.3% homology (FIG. 7) with the rat amino acid sequence.

The genes encoding the rat S10-87 and S10-95 receptors were transiently expressed in Cos-7 cells for pharmacological evaluation. Initial experiments using 5 nM [$^3$H]5-HT indicated that both S10-87 and S10-95 were serotonergic sites as demonstrated by the degree of specific binding and density of sites expressed in the transfected cells when compared against the mock transfected controls. Saturation analysis of S10-87 (CG7) was performed using 10 concentrations of [$^3$H]5-HT (1–100 nM) and yielded a Bmax of 1,938±399 fmol/mg of protein and a $K_d$ for [$^3$H]5-HT of 7.87±0.06 nM. The degree of specific binding at concentrations of [$^3$H]5-HT close to the $K_d$ ranged from 70–84% throughout the experimental series (including saturation and competition studies). Although the use of [$^3$H]5-HT as a radioligand to label 5-$HT_4$ receptors in brain tissue is not efficient due to the nonselectivity of the ligand, it became clear in the present studies using a homogeneous receptor population that [$^3$H]5-HT would label this particular receptor. In fact, [$^3$H]5-HT appears to be labelling the high affinity state of the 5-$HT_4$ receptor which is not unusual for the conditions upon which this receptor has been studied. Similar results using an agonist radioligand have been previously reported for the cloned 5-$HT_2$ receptor (Branchek et al., 1990).

A pharmacological binding profile of S10-87 and S10-95 (CG7 and CG8) was performed and demonstrated that this novel receptor was similar to the 5-$HT_4$ receptor as defined by functional assays in the literature (Bockaert et al., 1992). This is clearly shown in table 3 where the binding affinities of various serotonergic agents are displayed for S10. Notably, 5-HT and the tryptamine derivative 5-methoxytryptamine possessed high affinity. Furthermore, as previously reported for the 5-$HT_4$ receptor, benzamide derivatives including cisapride, BRL 24924 and zacopride bound with fairly high affinity to receptors expressed from the S10 gene. ICS 205930, a tropanyl-indole derivative, which has been reported to be an antagonist at both 5-$HT_3$ and 5-$HT_4$ receptors (Bockaert et al., 1992), also bound to these receptor sites. Compounds such as 8-hydroxy-2-(di-n-propylamino)tetralin, ketanserin, sumatriptan and 5-carboxyamidotryptamine were of low affinity having $K_i$ values estimated to be greater than 1 µM. This data would rule out S10 from belonging to other serotonergic receptor subfamilies such as 5-$HT_1$ and 5-$HT_2$. Taken together, the complete pharmacological profile also differentiates S10 from the related subtype 5-$HT_{4B}$ (U.S. Ser. No., 971,960, filed, Nov. 3, 1992, copending). Although some of the drugs tested also have good affinity for 5-$HT_3$ receptors, S10 is clearly a 5-$HT_4$ receptor based upon the binding data and the functional data demonstrating a positive-coupling to adenylate cyclase. Finally, a correlation plot for the binding affinities of 5-HT, cisapride, BRL 24924, zacopride, and ICS 205930 against their functional responses in adenylate cyclase assays from cultured mouse collicular neurons (Dumuis et al., 1989) yielded a correlation coefficient of 0.96 (FIG. 8). Thus, the rank order of potency for these key compounds also provides conclusive evidence that S10 encodes a 5-HT$_4$ receptor.

Figure 9:
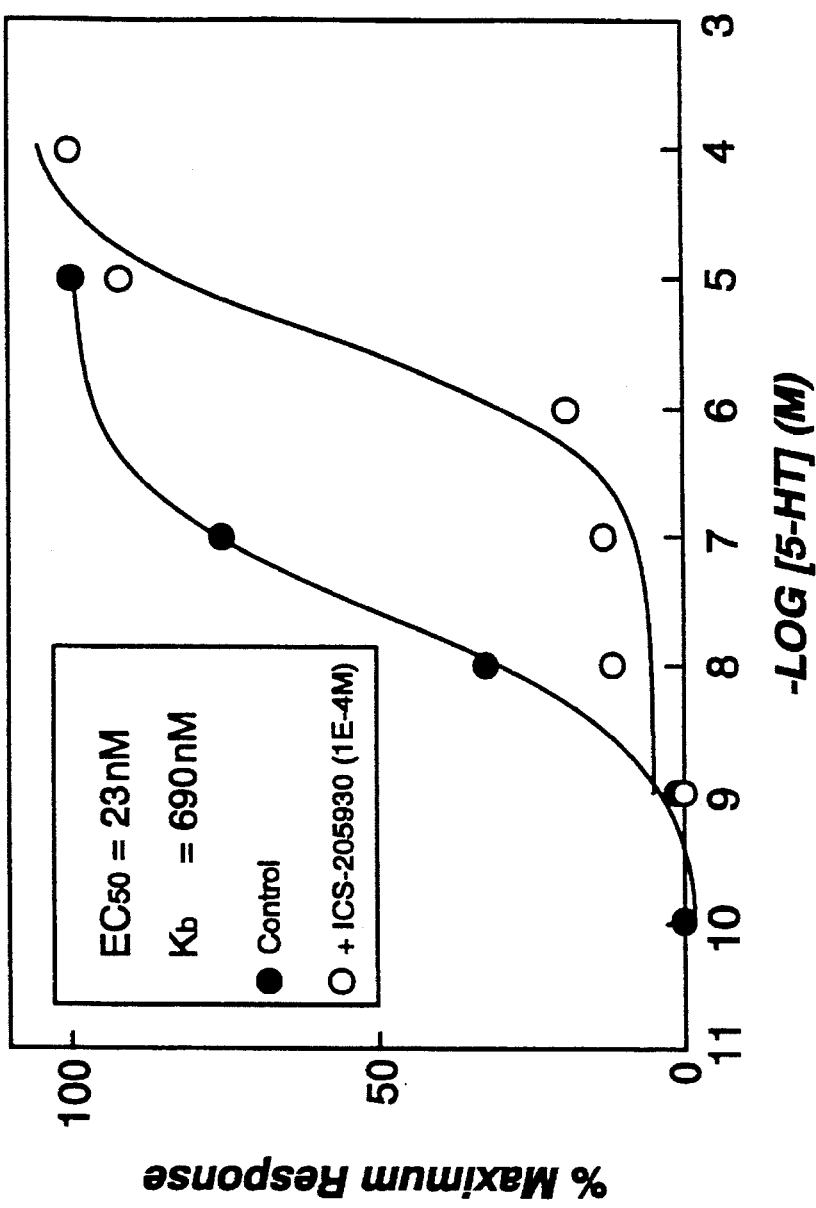
FIG. 9: Stimulation of cAMP production by 5-HT in transiently transfected Cos-7 cells expressing the cloned rat 5-HT$_{4A}$ (CG7) receptor and antagonism by ICS 205930. cAMP measurements on intact cells were as described under Methods and Materials. Each data point represents the mean of triplicates from a single experiment representative of at least 2 others. The vertical bars indicate S.E.M. Data are presented as percent maximum cAMP released by 5-HT (basal cAMP release: 0.020±0.002 pmol/ml/10 min; maximum cAMP release: 0.42±0.03 pmol/ml/10 min).
Figure 10:
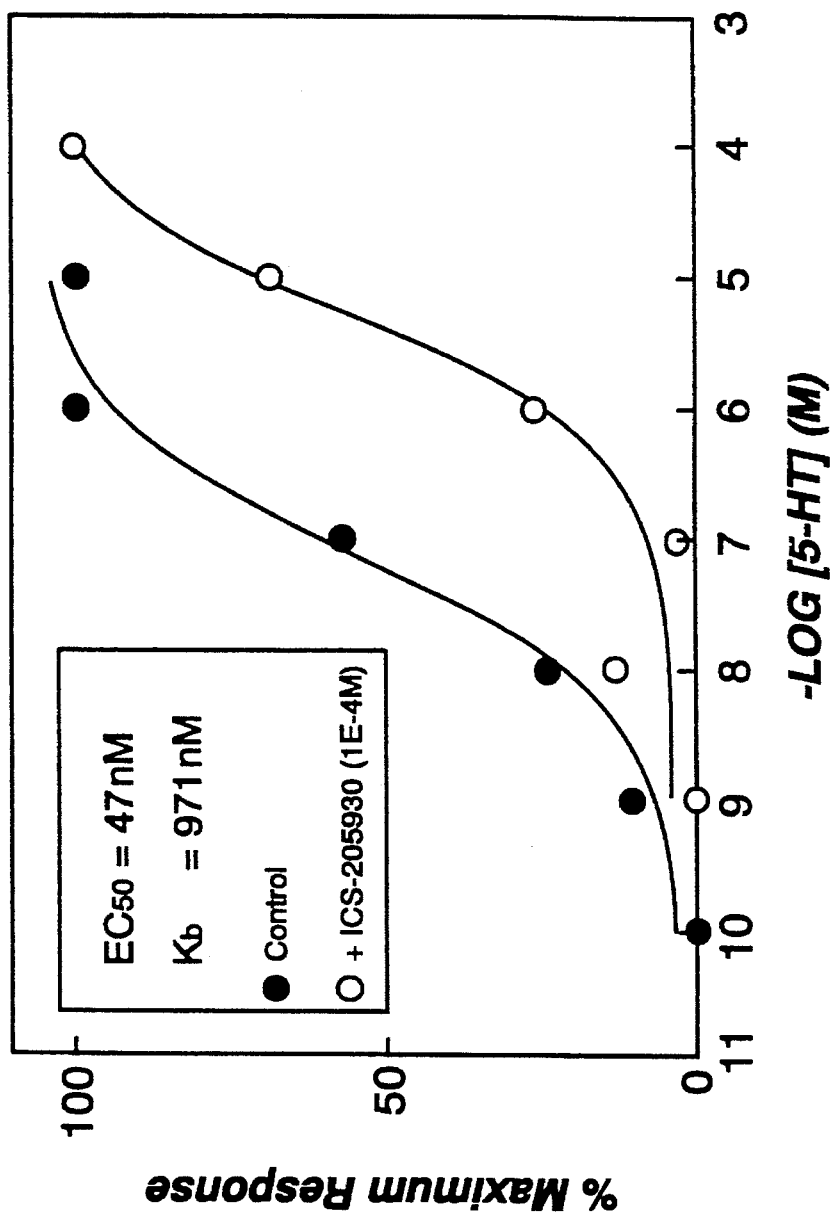
FIG. 10: Stimulation of cAMP production by 5-HT in transiently transfected Cos-7 cells expressing the cloned rat 5-HT$_{4A}$ (CG8) receptor and antagonism by ICS 205930. CAMP measurements on intact cells were as described under Methods and Materials. Each data point represents the mean of triplicates from a single experiment representative of at least two others. The vertical bars indicate S.E.M. Data are presented as percent maximum cAMP released by 5-HT (basal cAMP release: 0.023±0.004 pmol/ml/10 min; maximum cAMP release: 0.57±0.04 pmol/ml/10 min).

To examine the ability of S10 clone to couple to adenylate cyclase, Cos-7 cells transiently expressing S10 were tested for the ability to exhibit an increase in basal cAMP release or a decrease in FSK-stimulated cAMP response. 5-HT (1 µM) had no effect on either basal or FSK-stimulated adenylate cyclase activity in untransfected or mock-transfected Cos-7 cells (data not shown), indicating that endogenous cyclase-coupled serotonin receptors are not present in untransfected cells. Preliminary studies were carried out by adding only one dose of various drugs in triplicate. Addition of 5-HT (1 µM) to this system caused stimulation of basal cAMP release (CG7=0.020±0.002; CG8=0.023±0.004 pmol/ml/10 min) by about 30 fold for each clone; no inhibition of either the basal or FSK-stimulated cAMP release was observed. On the contrary, addition of 10 µM FSK together with 1 µM 5-HT stimulated cAMP accumulation about 10-fold more than either agent alone (data not shown). For various compounds, full dose-response curves were determined for both clones and the data are summarized in table 4. 5-HT caused a concentration-dependent stimulation of basal adenylate cyclase activity with mean EC$_{50}$s of 26±3 and 51±7 nM and E$_{max}$s of 2,107 and 2,598% basal cAMP release for CG7 and CG8 respectively (FIGS. 9 and 10). Among the tryptamine derivatives tested, 5-MeOT was approximately equipotent with 5-HT in both clones, whereas α-Me-5-HT and 5-CT were about 10 and 200 times respectively less potent than 5-HT at CG7. On the other hand, the latter two compounds displayed approximately 20 and 30 fold lower affinity than 5-HT respectively for CG8. The 2-methoxy-4-amino-5-chloro-substituted benzamides (cisapride, BRL-249245 and zacopride) were less potent agonists than 5-HT in stimulating basal cAMP release and displayed different rank order of potency for CG7 and CG8. As indicated in table 4 using CG7, cisapride, BRL-24924 and zacopride exhibited approximately 10, 30 and 100 fold lower potency than 5-HT respectively, whereas at CG8 these compounds had almost equal affinity. Thus, although not different in binding properties, these subtle differences in affinity in functional assays of the two "variants" (CG7 and CG8) indicate the potential to develop separate therapeutic entities for each separate target. All the agonists tested acted as full agonists with the exception of cisapride, BRL-24924 and zacopride, which also displayed antagonist activity and were therefore partial agonists at both clones, with intrinsic activities ranging between 0.85 and 1.4 (Table 4). ICS-205-930 (100 µM) had similar effect at the two clones and was found to be a silent antagonist causing parallel dextral shifts in the concentration effect curve of 5-HT without altering the maximum response significantly. The estimated K$_B$ value for ICS-205-930 was not significantly different between the two clones (CG7= 962±244 nM; CG8=607±30 nM). Responses to 5-HT were not affected by spiperone or methiothepin (10 µM) in either clone.

DISCUSSION

We have identified two cDNA clones encoding the pharmacologically-defined 5-HT$_4$ receptor. This receptor is expressed at low levels in rat brain if we consider its frequency in the cDNA library (≦1:10$^6$). Surprisingly, two receptors differing in their carboxy-terminus regions have been isolated. Since the 3' untranslated nucleotide sequences are also different, these two receptors could be encoded by two different genes or could arise by alternative splicing of pre-mRNA. These two receptors (S10-87 and S10-95) are differentially expressed in rat brain and the physiological relevance of the S10-87 receptor being expressed only in striatum remains to be determined.

The pharmacology binding profile and the functional coupling obtained from cells expressing S10 clones indicate that these genes both encode a pharmacologically-defined 5-HT$_4$ receptor. The cloned rat CG7 and CG8 genes transiently expressed in Cos-7 cells coupled to stimulation of adenylate cyclase. The magnitude of this response (~20–25 fold) was large. With the exception of 5-MeOT, agonist potencies determined from functional assays were less than expected from K$_i$ values obtained from binding assays using [$^3$H]5-HT. Could this result be due to the possibility that the dose of [$^3$H]5-HT used in binding assays measures only the high affinity site of agonists? This is not likely, as it would not account for the data obtained with ICS-205-930 which is a silent antagonist in the present system displaying approximately 6 (CG8) and 10 (CG7) fold lower affinity in the functional assay as compared to the binding experiments. It is more likely that differences in experimental conditions used in binding assays compared with those used in the functional assays (such as membrane vs. cells, buffers and extent of equilibrium achieved) accounts for these differences.

5-HT responses were resistant to blockade by methiothepin and spiperone (10 µM). As the concentration of these agents exceed their equilibrium dissociation constants for their respective receptor sites by 10–100 fold, it seems that 5-HT$_1$-like (5-HT$_{1A}$, 5-HT$_{1B}$, 5-HT$_{1C}$, 5-HT$_{1D}$, 5-HT$_{1E}$, 5-HT$_{1F}$), 5-HT$_2$ and 5-HT$_{4B}$ receptors can be ruled out. In addition, the weak agonistic activity of 5-CT relative to 5-HT further supports the notion that 5-HT$_1$-like receptors are probably not involved (Bradley, 1986). The results obtained with the indole agonists reflect those reported in the 5-HT$_4$ receptor in both the CNS and the periphery (Dumuis et al., 1988; Craig and Clarke, 1990; Eglen et al., 1990; Baxter, Craig and Clarke, 1991). The substituted benzamides, cisapride, BRL-24924 and zacopride acted as partial agonists. Although the benzamides also possess affinity for 5-HT$_3$ receptors, they lack intrinsic efficacy (Schuurkes et al., 1985; Sanger and King, 1988). Furthermore, the affinity of ICS-205- 930 for antagonism of 5-HT response at S10 is 1-3 orders of magnitude lower than that at 5-HT$_3$ receptors (Richardson et al., 1985) and therefore indicates a binding site different from 5-HT$_3$ receptor.

All the unique pharmacological characteristics described above define the S10 genes as adenylate cyclase stimulatory "5-HT$_4$" receptors reported in the literature that are expressed in the ileum (Craig and Clarke, 1990), hippocampus (Shenker et al., 1987), esophagus (Baxter et al., 1991), embryo colliculi neurons (Dumius et al., 1988), atrium (Kaumann et al., 1990), adrenal (Lefebvre et al., 1992) and bladder (Corsi et al., 1991), and distinguish these clones from all other cloned subtypes of 5-HT receptor. Although the binding profile of CG7 and CG8 were identical (Table 3), some differences in agonist potency (benzamides in particular) were observed between them in the functional assays. This is not surprising since the amino acid sequences of these two clones are identical, apart from the cytoplasmic carboxy tail, a region that is important for G protein-coupling, where the CG8 receptor carries an extra phosphorylation site. Cisapride, BRL-24924 and zacopride had similar affinities at CG8 whereas BRL-24924 and zacopride displayed approximately 4 and 15 fold lower affinity than cisapride at CG7 clone for stimulation of adenylate cyclase. It is noteworthy that tissue differences in the potency of benzamides have been reported (Baxter et al., 1991) and whether this reflects a heterogeneity of $5\text{-}HT_4$ receptors remains to be investigated.

The cloning and expression of genes encoding $5\text{-}HT_4$ receptors allows, for the first time, the ability to develop subtype selective drugs using radioligand binding assays. It will further provide definitive answers to whether there are significant species differences in the pharmacology of $5\text{-}HT_4$ receptors. In addition, the intrinsic activity of drugs can be determined from measures of adenylate cyclase activation in these transfected cells. So far, native tissue preparations have shown great disparity in agonist activity. $5\text{-}HT_4$ receptors have been implicated in a wide variety of functions. Existing drugs such as metaclopramide and cisapride appear to exert a large part of their action through $5\text{-}HT_4$ receptors (Taniyama et al., 1991; Meulemans and Schurkes, 1992; Flynn et al., 1992). Experience with these agents indicates a clear therapeutic role for $5\text{-}HT_4$ receptors in the gastrointestinal system for conditions including irritable bowel disease, postoperative ileus, diabetic gastroparesis, emesis, achalasia, hiatal hernia, and esophageal spasm. In addition, $5\text{-}HT_4$ receptors have been described functionally in the heart (Kaumann, 1992), adrenal (Lefebvre et al., 1992), and bladder (Corsi et al., 1991) indicating possible roles in cardiac rate and force of contraction, endocrine control of cortisol secretion, and urinary incontinence or spasticity. $5\text{-}HT_4$ receptors have also been described in the brain, particularly in areas such as the hippocampus, in which we have localized the gene encoding $5\text{-}HT_4$ receptors (S10-87), indicating a potential role in cognitive enhancement (Bockaert et al., 1992). As more specific pharmacological tools are developed, additional therapeutic indications will certainly be uncovered.

TABLE I

% TM homology of the S10 receptor with other 7 TM receptors

| SEROTONIN | ADRENERGIC | DOPAMINE | PEPTIDE |
|---|---|---|---|
| $5\text{-}HT_{1A}$ Hu 44 | Alpha-1A Hu 45 | $D_1$ Hu 43 | Subst K |
| $5\text{-}HT_{1D\alpha}$ Hu 40 | Alpha-1B Hu 43 | $D_2$ Hu 42 | Hu 25 |
| $5\text{-}HT_{1D\beta}$ Hu 41 | Alpha-1C Hu 40 | $D_3$ Rt 46 | TSH 27 |
| $5\text{-}HT_{1E}$ Hu 41 | Alpha-2A Hu 42 | $D_4$ Hu 45 | |
| $5\text{-}HT_{1F}$ Hu 41 | Alpha-2B Hu 40 | $D_5$ Hu 45 | |
| $5\text{-}HT_2$ Hu 42 | Alpha-2C Hu 40 | | |
| $5\text{-}HT_{1C}$ Hu 44 | | | |

TABLE I-continued

| | | HISTAMINE | MUSCARINIC |
|---|---|---|---|
| 5-HT Dro S 43 | Beta-1 Hu 46 | $H_1$ Bov 36 | m1 35 |
| 5-HT Dro $I_A$ 40 | Beta-2 Hu 44 | $H_2$ Hu 46 | |
| 5-HT Dro $I_B$ 41 | Beta-3 Hu 42 | | |
| $5\text{-}HT_{4B}$ Hu 44 | | | |

| | ADENOSINE |
|---|---|
| | A1 Rat 32 |
| | A2 Hu 31 |

TABLE 2

PCR localization of the S10 mRNA in 7 different part of the rat brain. The TM3-5 primers do not differentiate between clones S10-87 and S10-95. The S10-87 primers were designed from the nucleotide sequence coding for the TM 6 domain common to both receptors and for the carboxy terminus end specific to S10-87. In the same way, the S10-95 primers are specific for S10-95.

| Primers | Cortex | Cerebellum | Brain Stem | Hippocampus | Olfactory Bulb | Striatum | Thalamus |
|---|---|---|---|---|---|---|---|
| TM3-5 | + | – | + | + | + | + | + |
| S10-87 | ND | – | – | – | – | + | – |
| S10-95 | ND | – | + | + | + | + | + |

TABLE 3

Binding affinities of key ligands for the identification of S10 (CG7 and CG8) as a $5\text{-}HT_4$ receptor. Affinity constants (Ki; nM) of drugs competing for S10 labeled with 10 nM [3H]5-NT were determined to pharmacologically define the encoded receptor as $5\text{-}HT_4$ Ki (nM) values were calculated using the Cheng-Prusoff equation or estimated to be >1000 nM based upon one point displacements using a drug concentration of 1 uM. Affinity constants are expressed as the mean ±SEM (n ≥ 2). Ki values estimated to be >1000 were determined according to one point displacements studies at a concentration of 1 uM. (n = 2 except BRL 24924 tested at CG8: n = 1)

CHARACTERIZATION OF CLONE S-10
Saturation Analysis.     Kd = 7.87 ± 0.06 nM
                             Bmax = 1,938 fmol/ mg prot
Pharmacological profile:

| DRUG | CG7 | CG8 |
|---|---|---|
| 5-NT | 8.6 ± 0.6 | 6.4 ± 0.5 |
| Cisapride | 10.9 ± 0.3 | ND |
| 5-MeOT | 27.5 ± 5 | ND |
| BRL 24924 | 27.7 ± 5 | 21.1* |
| ICS 205930 | 115 ± 12 | 138 ± 26 |
| Zacopride | 130 ± 10 | 135 ± 5 |
| 8OHDPAT | >1000 | ND |
| Ketanserin | >1000 | ND |
| Sumatriptan | >1000 | ND |
| 5-CT | >1000 | ND |

*n = 1
ND = not determined

TABLE 4

Parmacological profile for the cAMP response using the human 5-HT$_{4A}$ (CG7 and CG8) receptor transiently expressed in Cos-7 cells, comparison with the binding data obtained with CG7 clone using [$^3$H]5-HT. cAMP measurement on intact cells were as described under Methods and Materials. EC$_{50}$ values (concentration producing the half-maximal effect were derived from the analysis of full dose-response curves. Maximum response produced by each drug was normalized to the 5-HT maximum response which is indicated as having an intrinsic activity of 1.0. Data are means ±S.E.M. of three separate experiments. The apparent dissociation constant of antagonist (K$_b$) (ICS 205930) was calculated according to the formula: K$_B$ = [B]/(A'/A)-1], where [B] is the concentration of antagonist, A' and A the EC$_{50}$ values of agonists measured respectively in the presence and in the absence of antagonist (Furchgott, 1972).

| Drug | EC$_{50}$ or K$_B$ (nM) | | I. A. | | K$_i$ (nM) | K$_i$ (nM) |
|---|---|---|---|---|---|---|
| | CG7 | CG8 | CG7 | CG8 | CG7 | CG8 |
| 5-MeOT | 21 ± 6 | 31 ± 13 | 1.0 | 1.0 | 27.5 ± 5 | ND |
| 5-HT | 26 ± 3 | 51 ± 7 | 1.0 | 1.0 | 8.6 ± 0.6 | 6.4 ± 0.5 |
| Cisapride | 191 ± 26 | 413 ± 31 | 1.2 | 1.4 | 10.9 ± 0.3 | ND |
| α-Me-5-HT | 250 ± 91 | 1,038 ± 31 | 0.90 | 1.0 | ND | ND |
| BRL-24924 | 736 ± 129 | 250 ± 25 | 1.1 | 0.9 | 27.7 ± 5 | 21 |
| Zacopride | 2,740 ± 274 | 239 ± 33 | 1.1 | 1.0 | 130 ± 10 | 136 ± 5 |
| 5-CT | 5,570 ± 808 | 1,411 ± 211 | 0.85 | 1.2 | >1,000 | ND |
| ICS-205930 | 962 ± 244 | 607 ± 30 | 0 | 0 | 115 ± 12 | 138 ± 26 |

ND, not determined.
Maximum response to 5-HT in Cos-7 cells transiently transfected with CG7 and CG8 genes was:
CG7 = 2,107 ± 52% of basal cAMP release
CG8 = 2,598 ± 154% of basal cAMP release
Cisapride, BRL-24924 and zacopride also had antagonist activity whereas ICS-205930 had no intrinsic agonist activity.

REFERENCES

Adham, N., P. Romanienko, P. Hartig, R. L. Weinshank, and T. Branchek. The rat 5-hydroxytryptamine$_{1B}$ receptor is the species homologue of the human 5-hydroxytryptamine$_{1D\beta}$ receptor. Mol. Pharmacol. 41:1–7 (1992).

Adham, N., H.-T. Kao, L. E. Schechter, J. Bard, M. Olsen, D. Urquhart, M. Durkin, P. R. Hartig, R. L. Weinshank, and T. A. Branchek. Cloning of a novel human serotonin receptor (5-HT1F): A fifth 5-HT$_1$ receptor subtype coupled to the inhibition of adenylate cyclase. Proc. Natl. Acad. Sci. USA, in press.

Bockaert, J., J. R. Fozard, A. Dumuis, and D. E. Clarke. The 5-HT$_4$ receptor: a place in the sun. Trends Pharmacol. Sci. 13:141–145 (1992).

Bockaert, J., M. Sebben, and A. Dumius. Pharmacological characterization of 5-hydroxytryptamine$_4$ (5-HT$_4$) receptors positivly coupled to adenylate cyclase in adult guineapig hippocampal membranes: effect of substituted benzamide derivatives. Mol. Pharmacol. 37:408–411 (1990).

Bradford, M. M. A rapid and sensitive method for the quantification of microgram quantities of protein utilizing the principle of protein-dye binding. Anal. Biochem. 72:248–254 (1976).

Bradley, P. B., G. Engel, W. Fenuik, J. R. Fozard, P. P. Humphrey et al. Proposals for the nomenclature of functional receptors for 5-hydroxytryptamine. Neuropharmacology 25:563–576 (1986).

Branchek, T., N. Adham, M. Macchi, H.-T. Kao, and P. R. Hartig. [$^3$H]-DOB (4-bromo-2,5-dimethoxyphenylisopropylamine) and [$^3$H]ketanserin label two affinity states of the cloned human 5-hydroxytryptamine$_2$ receptor. Mol. Pharmacol. 38:604–609 (1990).

Capecchi, M. R., Science 244:1288–1292 (1989).

Chirgwin, J. M., A. E. Przybyla, R. J. MacDonald, and W. J. Rutter. Isolation of biologically active ribonucleic acid from sources enriched in ribonuclease. Biochemistry 18:5294 (1979).

Cohen, J. S., Trends in Pharm. Sci. 10:435 (1989)

Cushing, D., and M. L. Cohen. Comparison of the serotonin receptors that mediate smooth muscle contraction in canine and porcine coronary artery. J. Pharmacol. Exp. Ther. 261:856–861 (1992).

Demchyshyn, L., R. K. Sunahara, K. Miller, M. Teitler, B. J. Hoffman, J. L. Kennedy, P. Seeman, H. H. M. Van Tol, and H. B. Niznik. A human serotonin 1D receptor variant (5-HT1Dβ) encoded by an intronless gene on chromosome 6. Proc. Natl. Acad. Sci. USA 89:5522–5526 (1992).

Dumuis, A., R. Bouhelal, M. Sebben, R. Cory, and J. Bockaert. A nonclassical 5-hydroxytryptamine receptor positively coupled with adenylate cyclase in the central nervous system. Mol. Pharmacol. 34:880–887 (1988).

Dumuis, A., M. Sebben, and J. Bockaert. (1989). The gastrointestinal prokinetic benzamide derivatives are agonists at the non-classical 5-HT receptor (5-HT$_4$) positively coupled to adenylate cyclase in neurons. Naunyn-Schmiedeberg's Arch. Pharmacol. 340:403–410 (1989).

Fargin, A., J. R. Raymond, M. J. Lohse, B. K. Kobilka, M. G. Caron, and R. J. Lefkowitz. The genomic clone G21, which resembles a β-adrenergic receptor sequence, encodes the human 5-HT$_{1A}$ receptor. Nature (Londo) 335:358–360 (1988).

Foquet, M., D. Hoyer, L. A. Pardo, A. Parekh, F. W. Kluxen, H. O. Kalkman, W. Stühmer, and H. Lübbert. Cloning and functional characterization of the rat stomach fundus serotonin receptor. EMBO J. 11(3):3481–3487 (1992).

Gubler, U., and B. J. Hoffman. A simple and very efficient method for generating cDNA libraries. Gene 25:263 (1983).

Hamblin, M. W., and M. A. Metcalf. Primary structure and functional characterization of a human 5-HT$_{1D}$-type serotonin receptor. Mol. Pharmacol. 40:143–148 (1991).

Hartig, P. R., H.-T. Kao, M. Macchi, N. Adham, J. Zgombick, R. Weinshank, and T. Branchek. The molecular biology of serotonin receptors: an overview. Neuropsychopharmacol. 3:335–347 (1990).

Herrick-Davis, K. and M. Titeler. Detection and characterization of the serotonin 5-HT$_{1D}$ receptor in rat and human brain. J. Neurochem. 50:1624–1631 (1988).

Hogan, B., et al., Manipulating the Mouse Embryo, A Laboratory Manual, Cold Spring Laboratory (1986).

Jin, H., D. Oksenberg, A. Ashkenazi, S. J. Peroutka, A. M. V. Duncan, R. Rozmahel, Y. Yang, G. Mengod, J. M. Palacios, and B. F. O'Dowd. Characterization of the human 5-hydroxytryptamine$_{1B}$ receptor. J. Biol. Chem. 267:5735–5738 (1992).

Kobilka, B. K., T. Frielle, S. Collins, T. Yang-Feng, T. S. Kobilka, U. Francke, R. J. Lefkowitz, and C. G. Caron. An intronless gene encoding a potential member of the family of receptors coupled to guanine nucleotide regulatory proteins. Nature 329:75–77 (1988).

Levy, F. O., T. Gudermann, M. Birnbaumer, A. J. Kaumann, and L. Birnbaumer. Molecular cloning of a human gene (S31) encoding a novel serotonin receptor mediating inhibition of adenylyl cyclase. FEBS. Lett. 296:201–206 (1992).

Low, M. J., R. M. Lechan and R. E. Hammer, Science 231: 1002–1004 (1986).

Maniatis, T., E. F. Fritsch, and J. Sambrook, Molecular Cloning Manual, Cold Spring Harbor Laboratory, Cold Spring Harbor N.Y. (1982).

Maricq, A. V., A. V. Peterson, A. J. Brake, R. M. Myers, and D. Julius. Primary structure and functional expression of the 5-HT$_3$ receptor, a serotonin-gated ion channel. Science 254:432–436 (1991).

Maroteaux, L., F. Saudou, N. Amlaiky, U. Boschert, J. L. Plassat, R. Hen. Mouse 5-HT$_1$B serotonin receptor: cloning, functional expression, and localization in motor control centers. Proc. Natl. Acad. Sci. USA 89:3020–3024 (1992).

McAllister, G., A. Charlesworth, C. Snodin, M. S. Beer, A. J. Noble, D. N. Middlemiss, L. L. Iverson, and P. Whiting. Molecular cloning of a serotonin receptor from human brain (5-HT$_1$E); A fifth 5-HT1-like subtype. Proc. Natl. Acad. Sci. USA 89:5517–5521 (1992).

Miller, J., and R. N. Germain. Efficient cell surface expression of class II MHC molecules in the absence of associated invariant chain. J. Exp. Med. 164:1478–1489 (1986).

Mylecharane, E. and C. Phillips. Mechanisms of 5-hydroxytryptamine-induced vasodilation. In: The Peripheral Actions of 5-hydroxytryptamine, J. R. Fozard, ed. Oxford University Press, Oxford, pp. 147–181 (1989).

Oberdick, J., R. J. Smeyne, J. R. Mann, S. Jackson and J. I. Morgan, Science 248:223–226 (1990).

O'Dowd, B. F., M. Hnatowich, M. G. Caron, R. J. Lefkowitz, and M. Bouvier. Palmitoylation of the Human β$_2$-Adrenergic Receptor. J. Biol. Chem. 264:7564–7569 (1989).

Pritchett, D. B., A. W. J. Bach, M. Wozny, O. Taleb, R. Dal Toso, J. C. Shih, and P. H. Seeburg. Structure and functional expression of a cloned rat serotonin 5-HT-2 receptor. EMBO J. 7:4135–4140 (1988).

Sambrook, J., E. F. Fritsch, and T. Maniatis. In: Molecular Cloning: A Laboratory Manual, 2nd Edition, Cold Spring Harbor Laboratory, Cold Spring Harbor, N.Y. (1989).

Sarver, N., et al., Science 247:1222 (1990).

Shenker, A., S. Maayani, H. Weinstein, and J. P. Green. Pharmacological characterization of two 5-hydroxytryptamine receptors coupled to adenylate cyclase in guinea pig hippocampal membranes. Mol. Pharmacol. 31:357–367 (1987).

Trevethick, M. A., W. Feniuk, and P. P. A. Humphrey. 5-hydroxytryptamine induced relaxation of neonatal porcine vena cava in vitro. Life Sci. 35:477–486 (1984).

Warden, D., and H. V. Thorne. Infectivity of polyoma virus DNA for mouse embryo cells in presence of diethylaminoethyl-dextran. J. Gen. Virol. 3:371 (1968).

Weinshank, R. L., J. M. Zgombick, M. Macchi, N. Adham, H. Lichtblau, T. A. Branchek, and P. R. Hartig. Cloning, expression, and pharmacological characterization of a human α$_{2B}$-adrenergic receptor. Mol. Pharmacol. 38: 681–688 (1990).

Weinshank, R. L., J. M. Zgombick, M. Macchi, T. A. Branchek, and P. R. Hartig. The human serotonin 1D receptor is encoded by a subfamily of two distinct genes: 5-HT$_{1D\alpha}$ and 5-HT$_{1D\beta}$. Proc. Natl. Acad. Sci. USA 89:3630–3634 (1992a).

Weintraub, H. M., Scientific American, January (1990) p.40.

Zhao D., J. Yang, K. E. Jones, C. Gerald, Y. Suzuki, P. G. Hogan, W. W. Chin, and A. H. Tashjian, Jr. Molecular cloning of a cDNA encoding the thyrotropin-releasing hormone receptor and regulation of its mRNA in rat GH cells. Endocrinology. 130:3529–3536 (1992).

Zemlan, F. P., and E. F. Schwab. Characterization of a novel serotonin receptor subtype (5-HT$_{1S}$) in rat CNS: interaction with a GTP binding protein. J. Neurochem. 57:2092–2099 (1991).

Zgombick, J. M., R. L. Weinshank, M. Macchi, L. E. Schechter, T. A. Branchek, and P. R Hartig. Expression and pharmacological characterization of a canine 5-hydroxytryptamine$_{1D}$ receptor subtype. Mol. Pharmacol. 40:1036–1042 (1991).

Zgombick, J. M., L. E. Schechter, M. Macchi, P. R. Hartig, T. A. Branchek, and R. L. Weinshank. Human gene S31 encodes the pharmacologically defined serotonin 5-hydroytryptamine$_{1E}$ receptor. Mol. Pharmacol. 42:180–185 (1992).

Zimmer, A., and P. Gruss, Nature 338:150–153 (1989).

---

What is claimed is:

1. An isolated nucleic acid molecule encoding a mammalian 5-HT4A receptor having the amino acid sequence shown in FIG. 1 (Seq. I.D. No. 2).
2. A nucleic acid molecule of claim 1, wherein the nucleic acid molecule is a DNA molecule.
3. A DNA molecule of claim 2 wherein the DNA molecule is genomic DNA.
4. A DNA molecule of claim 2 wherein the DNA molecule is a cDNA molecule.
5. A vector comprising a cDNA molecule of claim 4.
6. A vector of claim 5 adapted for expression in a bacterial cell which comprises the regulatory elements necessary for expression of the cDNA encoding a 5-HT$_{4A}$ receptor in the bacterial cell so located relative to the cDNA as to permit expression thereof.
7. A vector of claim 5 adapted for expression in a yeast cell which comprises the regulatory elements necessary for the expression of the cDNA encoding a 5-HT$_{4A}$ receptor in the yeast cell so located relative to the cDNA as to permit expression thereof.
8. A vector of claim 5 adapted for expression in a mammalian cell which comprises the regulatory elements necessary for expression of the cDNA encoding a 5-HT$_{4A}$ receptor in the mammalian cell so located relative to the cDNA as to permit expression thereof.
9. A plasmid vector of claim 5.
10. A plasmid of claim 9 adapted for expression in a mammalian cell which comprises the regulatory elements necessary for expression of the DNA in the mammalian cell so located relative to the DNA encoding a 5-HT$_{4A}$ receptor as to permit expression thereof.
11. A plasmid of claim 10 designated PcEXV-S10-87 (ATCC Accession No. 75390).
12. A mammalian cell comprising the plasmid of claim 9.
13. A mammalian cell of claim 12, wherein the mammalian cell is an LM (tk−) cell.
14. An isolated nucleic acid molecule encoding a mammalian 5-HT4A receptor having the amino acid sequence shown in FIG. 2 (Seq. I.D. No. 4).
15. A nucleic acid molecule of claim 14, wherein the nucleic acid molecule is a DNA molecule.
16. A DNA molecule of claim 15 wherein the DNA molecule is derived from genomic DNA.
17. A DNA molecule of claim 15, wherein the DNA molecule is a cDNA molecule.
18. A vector comprising a cDNA molecule of claim 17.
19. A vector of claim 18 adapted for expression in a bacterial cell which comprises the regulatory elements necessary for expression of the cDNA encoding a 5-HT$_{4A}$ receptor in the bacterial cell so located relative to the cDNA as to permit expression thereof.
20. A vector of claim 18 adapted for expression in a yeast cell which comprises the regulatory elements necessary for the expression of the cDNA encoding a 5-HT$_{4A}$ receptor in the yeast cell so located relative to the cDNA as to permit expression thereof.
21. A vector of claim 18 adapted for expression in a mammalian cell which comprises the regulatory elements necessary for expression of the cDNA encoding a 5-HT$_{4A}$ receptor in the mammalian cell so located relative to the cDNA as to permit expression thereof.
22. A plasmid vector of claim 18.
23. A plasmid of claim 22 adapted for expression in a mammalian cell which comprises the regulatory elements necessary for expression of the DNA in the mammalian cell so located relative to the DNA encoding a 5-HT$_{4A}$ receptor as to permit expression thereof.
24. A plasmid of claim 23 designated pcEXV-S10-95 (ATCC Accession No. 75391).
25. A mammalian cell comprising the plasmid of claim 24.
26. A mammalian cell of claim 24, wherein the mammalian cell is an LM (tk−) cell.

* * * * *

UNITED STATES PATENT AND TRADEMARK OFFICE
CERTIFICATE OF CORRECTION

PATENT NO. : 5,472,866
DATED : December 5, 1995
INVENTOR(S) : Christophe Gerald, Paul R. Hartig, Theresa A. Branchek, Richard L. Weinshank It is certified that error appears in the above-identified patent and that said Letters Patent is hereby corrected as shown below:

Col.4, line 42, change "FIG.4" to --FIG.4A-4C--
Col.5, line 26, change "CAMP" to --cAMP--
Col. 7, line 47, change "mantmalian" to --mammalian--
Col. 18, line 44, change "in vivo" to "*in vivo*"
Col.21, line 10, change "Amplifioation" to --Amplification--
  line 15, change "CUCTGGA" to --CICTGGA--
  line 24, change "using on" to --on--
  line 25, change "gel ethidium" to --gel using ethidium--
  line 58, change "2.5x10⁴" to --2.5 to 5 x 10⁴--
Col.23, line 51, change "FIG.4)" to "FIG.4A-4C)--
Col.24, line 6, change "parts-of" to --parts of--
Col.27, line 59, change "Subst K" to --Subst K
Col.28, line 42, change "[3H]5-NT" to --[$^3$H]5-HT--
  line 54, change "5-NT" to --5-HT--
Col.29, line 10, change "$K_8$" to --$K_B$--
Col.31, line 33, change "5-HT$_1$B" to --5-HT$_{1B}$--
  line 40, change "5-HT$_1$E" to --5-HT$_{1E}$--
Col.59, line 20, change "5-HT4A" to --5-HT$_{4A}$--
Col.59, line 56, change "5-HT4A" to --5-HT$_{4A}$--

Signed and Sealed this

Eighth Day of September, 1998

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1642 base pairs
        ( B ) TYPE: nucleic acid
        ( C ) STRANDEDNESS: double
        ( D ) TOPOLOGY: unknown (ii) MOLECULE TYPE: cDNA (iii) HYPOTHETICAL: N (iv) ANTI-SENSE: N (vi) ORIGINAL SOURCE:
(F) TISSUE TYPE: brain (vii) IMMEDIATE SOURCE:
(A) LIBRARY: rat brain
(B) CLONE: S10-87

(ix) FEATURE:
(A) NAME/KEY: CDS
(B) LOCATION: 101..1261
(D) OTHER INFORMATION:

(xi) SEQUENCE DESCRIPTION: SEQ ID NO:1:

| | | | | | | |
|---|---|---|---|---|---|---|
| AGCCTTGCCG | AGCCTGGCTT | GGTTGGAAGG | AGGAGGATGC | TCTGCGTGCC | CAGGGTCCTG | 60 |
| TGGGCACTGA | CATCCAACGT | ACTCATGCCC | ATTCCTGTA | ATG GAC AGA CTT GAT | | 115 |
| | | | | Met Asp Arg Leu Asp | | |
| | | | | 1       5 | | |

```
GCT AAT GTG AGT TCC AAC GAG GGT TTC GGG TCT GTG GAG AAG GTC GTA    163
Ala Asn Val Ser Ser Asn Glu Gly Phe Gly Ser Val Glu Lys Val Val
            10              15              20

CTG CTC ACG TTC TTC GCA ATG GTT ATC CTG ATG GCC ATC CTG GGC AAC    211
Leu Leu Thr Phe Phe Ala Met Val Ile Leu Met Ala Ile Leu Gly Asn
        25              30              35

CTG CTG GTG ATG GTT GCT GTG TGC AGG GAC AGG CAG CTC AGG AAA ATA    259
Leu Leu Val Met Val Ala Val Cys Arg Asp Arg Gln Leu Arg Lys Ile
        40              45              50

AAA ACC AAT TAT TTC ATT GTG TCT CTT GCC TTT GCT GAT CTG CTG GTT    307
Lys Thr Asn Tyr Phe Ile Val Ser Leu Ala Phe Ala Asp Leu Leu Val
    55              60              65

TCG GTG CTG GTG AAT GCC TTC GGT GCC ATT GAG TTG GTC CAA GAC ATC    355
Ser Val Leu Val Asn Ala Phe Gly Ala Ile Glu Leu Val Gln Asp Ile
70              75              80              85

TGG TTT TAT GGG GAG ATG TTT TGC CTG GTC CGG ACC TCT CTG GAT GTC    403
Trp Phe Tyr Gly Glu Met Phe Cys Leu Val Arg Thr Ser Leu Asp Val
                90              95              100

CTA CTC ACC ACA GCA TCA ATT TTT CAC CTC TGC TGC ATT TCC CTG GAT    451
Leu Leu Thr Thr Ala Ser Ile Phe His Leu Cys Cys Ile Ser Leu Asp
            105             110             115

AGG TAT TAT GCC ATC TGC TGT CAA CCT TTG GTT TAT AGA AAC AAG ATG    499
Arg Tyr Tyr Ala Ile Cys Cys Gln Pro Leu Val Tyr Arg Asn Lys Met
        120             125             130

ACC CCT CTA CGC ATC GCA TTA ATG CTG GGA GGC TGC TGG GTC ATT CCC    547
Thr Pro Leu Arg Ile Ala Leu Met Leu Gly Gly Cys Trp Val Ile Pro
        135             140             145

ATG TTT ATA TCT TTT CTC CCC ATA ATG CAA GGC TGG AAC AAC ATC GGC    595
Met Phe Ile Ser Phe Leu Pro Ile Met Gln Gly Trp Asn Asn Ile Gly
150             155             160             165

ATA GTT GAT GTG ATA GAG AAA AGG AAA TTC AAC CAC AAC TCT AAC TCT    643
Ile Val Asp Val Ile Glu Lys Arg Lys Phe Asn His Asn Ser Asn Ser
            170             175             180

ACA TTC TGT GTC TTC ATG GTC AAC AAG CCC TAT GCC ATC ACC TGC TCT    691
Thr Phe Cys Val Phe Met Val Asn Lys Pro Tyr Ala Ile Thr Cys Ser
        185             190             195

GTG GTG GCC TTC TAC ATC CCG TTT CTC CTC ATG GTG CTG GCC TAT TAC    739
Val Val Ala Phe Tyr Ile Pro Phe Leu Leu Met Val Leu Ala Tyr Tyr
        200             205             210
```

```
CGT ATC TAT GTC ACT GCT AAG GAG CAT GCC CAG CAG ATC CAG ATG TTA     787
Arg Ile Tyr Val Thr Ala Lys Glu His Ala Gln Gln Ile Gln Met Leu
    215                 220                 225

CAA CGG GCA GGA GCC ACC TCT GAA AGC AGG CCC CAG ACA GCT GAC CAG   835
Gln Arg Ala Gly Ala Thr Ser Glu Ser Arg Pro Gln Thr Ala Asp Gln
230                 235                 240                 245

CAC AGC ACA CAT CGC ATG CGG ACA GAG ACC AAA GCA GCC AAG ACT TTA     883
His Ser Thr His Arg Met Arg Thr Glu Thr Lys Ala Ala Lys Thr Leu
                250                 255                 260

TGT GTC ATC ATG GGC TGC TTC TGT TTC TGC TGG GCC CCC TTC TTT GTC     931
Cys Val Ile Met Gly Cys Phe Cys Phe Cys Trp Ala Pro Phe Phe Val
            265                 270                 275

ACC AAT ATT GTG GAC CCT TTC ATA GAC TAC ACT GTG CCC GAG AAG GTG     979
Thr Asn Ile Val Asp Pro Phe Ile Asp Tyr Thr Val Pro Glu Lys Val
        280                 285                 290

TGG ACT GCT TTC CTC TGG CTT GGC TAT ATC AAT TCA GGG TTG AAC CCT    1027
Trp Thr Ala Phe Leu Trp Leu Gly Tyr Ile Asn Ser Gly Leu Asn Pro
    295                 300                 305

TTT CTC TAT GCC TTC TTG AAT AAG TCT TTC AGA CGT GCC TTC CTT ATC    1075
Phe Leu Tyr Ala Phe Leu Asn Lys Ser Phe Arg Arg Ala Phe Leu Ile
310                 315                 320                 325

ATC CTC TGC TGT GAT GAT GAG CGC TAC AAA AGA CCC CCC ATT CTG GGC    1123
Ile Leu Cys Cys Asp Asp Glu Arg Tyr Lys Arg Pro Pro Ile Leu Gly
                330                 335                 340

CAG ACT GTC CCC TGT TCA ACC ACA ATT AAT GGA TCC ACT CAT GTG        1171
Gln Thr Val Pro Cys Ser Thr Thr Ile Asn Gly Ser Thr His Val
            345                 350                 355

CTA AGG TAT ACA GTT TTG CAT AGT GGT CAA CAC CAG GAA CTG GAG AAG    1219
Leu Arg Tyr Thr Val Leu His Ser Gly Gln His Gln Glu Leu Glu Lys
        360                 365                 370

TTG CCC ATA CAC AAT GAC CCA GAG TCC CTG GAA TCA TGC TTT            1261
Leu Pro Ile His Asn Asp Pro Glu Ser Leu Glu Ser Cys Phe
375                 380                 385

TGATTGAAGA CGTGGCTTGC CTTTAGCGGT TCATCCCATC TGTGTCTGCA TGAACAGGTT  1321

ACTATGGAAT CACTCCTGAC TCTGGGCATC ACCAGTGAAG CATGAGCATG GTGAGGCAGG  1381

GTCCGGTGAA GGTGCACAGA GGACAGCATT GAGTGGGACC TGAACCCAGC ACATTAAGGA  1441

TTTCAGAACC GTGTGGGGAT TTGAGATGTC ATCAGACCCA GTGTCTTACC CAGAGCCCAA  1501

CTGGCACCTC CCATTCCACG CTGACATGTG GTCAGTCTTT GCTCACACCT CTCCAGGGGC  1561

AGGAGCTGAC TACCTCCTAA TGTGGTGGGG AGCTCTTAAT TGTGTGGAAG TTCAGTCATT  1621

CATTGGTGGA CAGTCTCGCT G                                           1642
```

( 2 ) INFORMATION FOR SEQ ID NO:2:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Arg Leu Asp Ala Asn Val Ser Ser Asn Glu Gly Phe Gly Ser
 1               5                  10                  15

Val Glu Lys Val Val Leu Leu Thr Phe Phe Ala Met Val Ile Leu Met
            20                  25                  30

Ala Ile Leu Gly Asn Leu Leu Val Met Val Ala Val Cys Arg Asp Arg
        35                  40                  45
```

| Gln | Leu | Arg | Lys | Ile | Lys | Thr | Asn | Tyr | Phe | Ile | Val | Ser | Leu | Ala | Phe |
|---|---|---|---|---|---|---|---|---|---|---|---|---|---|---|---|
| | 50 | | | | 55 | | | | | 60 | | | | | |
| Ala | Asp | Leu | Leu | Val | Ser | Val | Leu | Val | Asn | Ala | Phe | Gly | Ala | Ile | Glu |
| 65 | | | | 70 | | | | | 75 | | | | | | 80 |
| Leu | Val | Gln | Asp | Ile | Trp | Phe | Tyr | Gly | Glu | Met | Phe | Cys | Leu | Val | Arg |
| | | | | 85 | | | | | 90 | | | | | 95 | |
| Thr | Ser | Leu | Asp | Val | Leu | Leu | Thr | Thr | Ala | Ser | Ile | Phe | His | Leu | Cys |
| | | | 100 | | | | | 105 | | | | | 110 | | |
| Cys | Ile | Ser | Leu | Asp | Arg | Tyr | Tyr | Ala | Ile | Cys | Cys | Gln | Pro | Leu | Val |
| | | 115 | | | | | 120 | | | | | 125 | | | |
| Tyr | Arg | Asn | Lys | Met | Thr | Pro | Leu | Arg | Ile | Ala | Leu | Met | Leu | Gly | Gly |
| | 130 | | | | | 135 | | | | | 140 | | | | |
| Cys | Trp | Val | Ile | Pro | Met | Phe | Ile | Ser | Phe | Leu | Pro | Ile | Met | Gln | Gly |
| 145 | | | | | 150 | | | | | 155 | | | | | 160 |
| Trp | Asn | Asn | Ile | Gly | Ile | Val | Asp | Val | Ile | Glu | Lys | Arg | Lys | Phe | Asn |
| | | | | 165 | | | | | 170 | | | | | 175 | |
| His | Asn | Ser | Asn | Ser | Thr | Phe | Cys | Val | Phe | Met | Val | Asn | Lys | Pro | Tyr |
| | | | 180 | | | | | 185 | | | | | 190 | | |
| Ala | Ile | Thr | Cys | Ser | Val | Val | Ala | Phe | Tyr | Ile | Pro | Phe | Leu | Leu | Met |
| | | 195 | | | | | 200 | | | | | 205 | | | |
| Val | Leu | Ala | Tyr | Tyr | Arg | Ile | Tyr | Val | Thr | Ala | Lys | Glu | His | Ala | Gln |
| | 210 | | | | | 215 | | | | | 220 | | | | |
| Gln | Ile | Gln | Met | Leu | Gln | Arg | Ala | Gly | Ala | Thr | Ser | Glu | Ser | Arg | Pro |
| 225 | | | | | 230 | | | | | 235 | | | | | 240 |
| Gln | Thr | Ala | Asp | Gln | His | Ser | Thr | His | Arg | Met | Arg | Thr | Glu | Thr | Lys |
| | | | | 245 | | | | | 250 | | | | | 255 | |
| Ala | Ala | Lys | Thr | Leu | Cys | Val | Ile | Met | Gly | Cys | Phe | Cys | Phe | Cys | Trp |
| | | | 260 | | | | | 265 | | | | | 270 | | |
| Ala | Pro | Phe | Phe | Val | Thr | Asn | Ile | Val | Asp | Pro | Phe | Ile | Asp | Tyr | Thr |
| | | 275 | | | | | 280 | | | | | 285 | | | |
| Val | Pro | Glu | Lys | Val | Trp | Thr | Ala | Phe | Leu | Trp | Leu | Gly | Tyr | Ile | Asn |
| | 290 | | | | | 295 | | | | | 300 | | | | |
| Ser | Gly | Leu | Asn | Pro | Phe | Leu | Tyr | Ala | Phe | Leu | Asn | Lys | Ser | Phe | Arg |
| 305 | | | | | 310 | | | | | 315 | | | | | 320 |
| Arg | Ala | Phe | Leu | Ile | Ile | Leu | Cys | Cys | Asp | Asp | Glu | Arg | Tyr | Lys | Arg |
| | | | | 325 | | | | | 330 | | | | | 335 | |
| Pro | Pro | Ile | Leu | Gly | Gln | Thr | Val | Pro | Cys | Ser | Thr | Thr | Thr | Ile | Asn |
| | | | 340 | | | | | 345 | | | | | 350 | | |
| Gly | Ser | Thr | His | Val | Leu | Arg | Tyr | Thr | Val | Leu | His | Ser | Gly | Gln | His |
| | | 355 | | | | | 360 | | | | | 365 | | | |
| Gln | Glu | Leu | Glu | Lys | Leu | Pro | Ile | His | Asn | Asp | Pro | Glu | Ser | Leu | Glu |
| | 370 | | | | | 375 | | | | | 380 | | | | |
| Ser | Cys | Phe | | | | | | | | | | | | | |
| 385 | | | | | | | | | | | | | | | |

( 2 ) INFORMATION FOR SEQ ID NO:3:

( i ) SEQUENCE CHARACTERISTICS:
        ( A ) LENGTH: 1622 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: N ( i v ) ANTI-SENSE: N ( v i ) ORIGINAL SOURCE:
    ( F ) TISSUE TYPE: brain ( v i i ) IMMEDIATE SOURCE:
    ( A ) LIBRARY: rat brain
    ( B ) CLONE: S10-95

( i x ) FEATURE:
    ( A ) NAME/KEY: CDS
    ( B ) LOCATION: 50..1267
    ( D ) OTHER INFORMATION:

( x i ) SEQUENCE DESCRIPTION: SEQ ID NO:3:

```
AGGGTCCTGT GGGCACTGAC ATCCAACGTA CTCATGCCCA TTTCCTGTA ATG GAC                55
                                                         Met Asp
                                                           1

AGA CTT GAT GCT AAT GTG AGT TCC AAC GAG GGT TTC GGG TCT GTG GAG            103
Arg Leu Asp Ala Asn Val Ser Ser Asn Glu Gly Phe Gly Ser Val Glu
          5              10                  15

AAG GTC GTA CTG CTC ACG TTC TTC GCA ATG GTT ATC CTG ATG GCC ATC            151
Lys Val Val Leu Leu Thr Phe Phe Ala Met Val Ile Leu Met Ala Ile
     20                  25                  30

CTG GGC AAC CTG CTG GTG ATG GTT GCT GTG TGC AGG GAC AGG CAG CTC            199
Leu Gly Asn Leu Leu Val Met Val Ala Val Cys Arg Asp Arg Gln Leu
 35              40                  45                      50

AGG AAA ATA AAA ACC AAT TAT TTC ATT GTG TCT CTT GCC TTT GCT GAT            247
Arg Lys Ile Lys Thr Asn Tyr Phe Ile Val Ser Leu Ala Phe Ala Asp
              55                  60                      65

CTG CTG GTT TCG GTG CTG GTG AAT GCC TTC GGT GCC ATT GAG TTG GTC            295
Leu Leu Val Ser Val Leu Val Asn Ala Phe Gly Ala Ile Glu Leu Val
              70                  75                  80

CAA GAC ATC TGG TTT TAT GGG GAG ATG TTT TGC CTG GTC CGG ACC TCT            343
Gln Asp Ile Trp Phe Tyr Gly Glu Met Phe Cys Leu Val Arg Thr Ser
              85                  90                  95

CTG GAT GTC CTA CTC ACC ACA GCA TCA ATT TTT CAC CTC TGC TGC CTT            391
Leu Asp Val Leu Leu Thr Thr Ala Ser Ile Phe His Leu Cys Cys Leu
        100                 105                 110

TCC CTG GAT AGG TAT TAT GCC ATC TGC TGT CAA CCT TTG GTT TAT AGA            439
Ser Leu Asp Arg Tyr Tyr Ala Ile Cys Cys Gln Pro Leu Val Tyr Arg
115                 120                 125                 130

AAC AAG ATG ACC CCT CTA CGC ATC GCA TTA ATG CTG GGA GGC TGC TGG            487
Asn Lys Met Thr Pro Leu Arg Ile Ala Leu Met Leu Gly Gly Cys Trp
                135                 140                 145

GTC ATT CCC ATG TTT ATA TCT TTT CTC CCC ATA ATG CAA GGC TGG AAC            535
Val Ile Pro Met Phe Ile Ser Phe Leu Pro Ile Met Gln Gly Trp Asn
                150                 155                 160

AAC ATC GGC ATA GTT GAT GTG ATA GAG AAA AGG AAA TTC AAC CAC AAC            583
Asn Ile Gly Ile Val Asp Val Ile Glu Lys Arg Lys Phe Asn His Asn
            165                 170                 175

TCT AAC TCT ACA TTC TGT GTC TTC ATG GTC AAC AAG CCC TAT GCC ATC            631
Ser Asn Ser Thr Phe Cys Val Phe Met Val Asn Lys Pro Tyr Ala Ile
180                 185                 190

ACC TGC TCT GTG GTG GCC TTC TAC ATC CCG TTT CTC CTC ATG GTG CTG            679
Thr Cys Ser Val Val Ala Phe Tyr Ile Pro Phe Leu Leu Met Val Leu
195                 200                 205                 210

GCC TAT TAC CGT ATC TAT GTC ACT GCT AAG GAG CAT GCC CAG CAG ATC            727
Ala Tyr Tyr Arg Ile Tyr Val Thr Ala Lys Glu His Ala Gln Gln Ile
                215                 220                 225

CAG ATG TTA CAA CGG GCA GGA GCC ACC TCT GAA AGC AGG CCC CAG ACA            775
Gln Met Leu Gln Arg Ala Gly Ala Thr Ser Glu Ser Arg Pro Gln Thr
                230                 235                 240
```

| | | | | | | | | | | | | | | | | |
|---|---|---|---|---|---|---|---|---|---|---|---|---|---|---|---|---|
| GCT | GAC | CAG | CAC | AGC | ACA | CAT | CGC | ATG | CGG | ACA | GAG | ACC | AAA | GCA | GCC | 823 |
| Ala | Asp | Gln 245 | His | Ser | Thr | His | Arg 250 | Met | Arg | Thr | Glu | Thr 255 | Lys | Ala | Ala | |
| AAG | ACT | TTA | TGT | GTC | ATC | ATG | GGC | TGC | TTC | TGT | TTC | TGC | TGG | GCC | CCC | 871 |
| Lys | Thr 260 | Leu | Cys | Val | Ile | Met 265 | Gly | Cys | Phe | Cys | Phe 270 | Cys | Trp | Ala | Pro | |
| TTC | TTT | GTC | ACC | AAT | ATT | GTG | GAC | CCT | TTC | ATA | GAC | TAC | ACT | GTG | CCC | 919 |
| Phe 275 | Phe | Val | Thr | Asn | Ile 280 | Val | Asp | Pro | Phe | Ile 285 | Asp | Tyr | Thr | Val | Pro 290 | |
| GAG | AAG | GTG | TGG | ACT | GCT | TTC | CTC | TGG | CTT | GGC | TAT | ATC | AAT | TCA | GGG | 967 |
| Glu | Lys | Val | Trp | Thr 295 | Ala | Phe | Leu | Trp 300 | Leu | Gly | Tyr | Ile | Asn 305 | Ser | Gly | |
| TTG | AAC | CCT | TTT | CTC | TAT | GCC | TTC | TTG | AAT | AAG | TCT | TTC | AGA | CGT | GCC | 1015 |
| Leu | Asn | Pro | Phe 310 | Leu | Tyr | Ala | Phe | Leu 315 | Asn | Lys | Ser | Phe | Arg 320 | Arg | Ala | |
| TTC | CTT | ATC | ATC | CTC | TGC | TGT | GAT | GAT | GAG | CGC | TAC | AAA | AGA | CCC | CCC | 1063 |
| Phe | Leu | Ile 325 | Ile | Leu | Cys | Cys | Asp 330 | Asp | Glu | Arg | Tyr | Lys 335 | Arg | Pro | Pro | |
| ATT | CTG | GGC | CAG | ACT | GTC | CCC | TGT | TCA | ACC | ACA | ACC | ATT | AAT | GGA | TCC | 1111 |
| Ile | Leu 340 | Gly | Gln | Thr | Val | Pro 345 | Cys | Ser | Thr | Thr | Thr 350 | Ile | Asn | Gly | Ser | |
| ACT | CAT | GTG | CTA | AGG | GAT | ACA | GTG | GAA | TGT | GGT | GGC | CAA | TGG | GAG | AGT | 1159 |
| Thr 355 | His | Val | Leu | Arg | Asp 360 | Thr | Val | Glu | Cys | Gly 365 | Gly | Gln | Trp | Glu | Ser 370 | |
| CGG | TGT | CAC | CTC | ACA | GCA | ACT | TCT | CCT | TTG | GTG | GCT | GCT | CAG | CCA | GTG | 1207 |
| Arg | Cys | His | Leu | Thr 375 | Ala | Thr | Ser | Pro | Leu 380 | Val | Ala | Ala | Gln | Pro 385 | Val | |
| ATA | CGT | AGG | CCC | CAG | GAC | AAT | GAC | CTA | GAA | GAC | AGC | TGT | AGC | TTG | AAA | 1255 |
| Ile | Arg | Arg | Pro 390 | Gln | Asp | Asn | Asp | Leu 395 | Glu | Asp | Ser | Cys | Ser 400 | Leu | Lys | |
| AGA | AGC | CAG | TCC | TAAGCTGCTA | CTTCGGTGTA | TGTGGCTGCC | CCTGGCACTT | | | | | | | | | 1307 |
| Arg | Ser | Gln 405 | Ser | | | | | | | | | | | | | |

| | | | | |
|---|---|---|---|---|
| TGTTCTCCAA | GGCTTTCCAA | GAGCATGAGG | CAATCCACCC | TGGACTTCCC GCCACGATTC | 1367 |
| TAGCAGGCGG | TATTAGAGGA | AGTCAGGGGA | GAGAAGGGCT | TCCTCCTTAG CTTTCTGTTT | 1427 |
| CTCAACATTT | TCTCTTCCTG | GAGTCTCCAC | TCTTGCTTGG | TGGTCTCTGA AGTCCACGAC | 1487 |
| CCAGTCCCCT | TTTGCTGTCT | CCAGTCTGTC | TTGTAAATGT | TTACCGTGTT CGATTTTCAG | 1547 |
| TTTCCAAACA | TGCCTTCTTT | GAAGTGTCAT | CTTACGATAC | TGTCAAAACA TGTGCCTGTC | 1607 |
| TTGATCACAC | TTCTT | | | | 1622 |

( 2 ) INFORMATION FOR SEQ ID NO:4:

( i ) SEQUENCE CHARACTERISTICS:
        ( A ) LENGTH: 406 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Asp | Arg | Leu | Asp 5 | Ala | Asn | Val | Ser | Ser 10 | Asn | Glu | Gly | Phe | Gly Ser 15 |
| Val | Glu | Lys | Val 20 | Val | Leu | Leu | Thr | Phe 25 | Phe | Ala | Met | Val | Ile 30 | Leu Met |
| Ala | Ile | Leu 35 | Gly | Asn | Leu | Leu | Val 40 | Met | Val | Ala | Val | Cys 45 | Arg | Asp Arg |
| Gln | Leu | Arg | Lys | Ile | Lys | Thr | Asn | Tyr | Phe | Ile | Val | Ser | Leu | Ala Phe |

|     |     |     |     |     | 50  |     |     |     |     | 55  |     |     |     |     | 60  |
| --- | --- | --- | --- | --- | --- | --- | --- | --- | --- | --- | --- | --- | --- | --- | --- |
| Ala | Asp | Leu | Leu | Val | Ser | Val | Leu | Val | Asn | Ala | Phe | Gly | Ala | Ile | Glu |
| 65  |     |     |     |     | 70  |     |     |     |     | 75  |     |     |     |     | 80  |
| Leu | Val | Gln | Asp | Ile | Trp | Phe | Tyr | Gly | Glu | Met | Phe | Cys | Leu | Val | Arg |
|     |     |     |     | 85  |     |     |     |     | 90  |     |     |     |     | 95  |     |
| Thr | Ser | Leu | Asp | Val | Leu | Leu | Thr | Thr | Ala | Ser | Ile | Phe | His | Leu | Cys |
|     |     |     | 100 |     |     |     |     | 105 |     |     |     |     | 110 |     |     |
| Cys | Leu | Ser | Leu | Asp | Arg | Tyr | Tyr | Ala | Ile | Cys | Cys | Gln | Pro | Leu | Val |
|     |     | 115 |     |     |     |     | 120 |     |     |     |     | 125 |     |     |     |
| Tyr | Arg | Asn | Lys | Met | Thr | Pro | Leu | Arg | Ile | Ala | Leu | Met | Leu | Gly | Gly |
|     | 130 |     |     |     |     | 135 |     |     |     |     | 140 |     |     |     |     |
| Cys | Trp | Val | Ile | Pro | Met | Phe | Ile | Ser | Phe | Leu | Pro | Ile | Met | Gln | Gly |
| 145 |     |     |     |     | 150 |     |     |     |     | 155 |     |     |     |     | 160 |
| Trp | Asn | Asn | Ile | Gly | Ile | Val | Asp | Val | Ile | Glu | Lys | Arg | Lys | Phe | Asn |
|     |     |     |     | 165 |     |     |     |     | 170 |     |     |     |     | 175 |     |
| His | Asn | Ser | Asn | Ser | Thr | Phe | Cys | Val | Phe | Met | Val | Asn | Lys | Pro | Tyr |
|     |     |     | 180 |     |     |     |     | 185 |     |     |     |     | 190 |     |     |
| Ala | Ile | Thr | Cys | Ser | Val | Val | Ala | Phe | Tyr | Ile | Pro | Phe | Leu | Leu | Met |
|     |     | 195 |     |     |     |     | 200 |     |     |     |     | 205 |     |     |     |
| Val | Leu | Ala | Tyr | Tyr | Arg | Ile | Tyr | Val | Thr | Ala | Lys | Glu | His | Ala | Gln |
|     | 210 |     |     |     |     | 215 |     |     |     |     | 220 |     |     |     |     |
| Gln | Ile | Gln | Met | Leu | Gln | Arg | Ala | Gly | Ala | Thr | Ser | Glu | Ser | Arg | Pro |
| 225 |     |     |     |     | 230 |     |     |     |     | 235 |     |     |     |     | 240 |
| Gln | Thr | Ala | Asp | Gln | His | Ser | Thr | His | Arg | Met | Arg | Thr | Glu | Thr | Lys |
|     |     |     |     | 245 |     |     |     |     | 250 |     |     |     |     | 255 |     |
| Ala | Ala | Lys | Thr | Leu | Cys | Val | Ile | Met | Gly | Cys | Phe | Cys | Phe | Cys | Trp |
|     |     |     | 260 |     |     |     |     | 265 |     |     |     |     | 270 |     |     |
| Ala | Pro | Phe | Phe | Val | Thr | Asn | Ile | Val | Asp | Pro | Phe | Ile | Asp | Tyr | Thr |
|     |     | 275 |     |     |     |     | 280 |     |     |     |     | 285 |     |     |     |
| Val | Pro | Glu | Lys | Val | Trp | Thr | Ala | Phe | Leu | Trp | Leu | Gly | Tyr | Ile | Asn |
|     | 290 |     |     |     |     | 295 |     |     |     |     | 300 |     |     |     |     |
| Ser | Gly | Leu | Asn | Pro | Phe | Leu | Tyr | Ala | Phe | Leu | Asn | Lys | Ser | Phe | Arg |
| 305 |     |     |     |     | 310 |     |     |     |     | 315 |     |     |     |     | 320 |
| Arg | Ala | Phe | Leu | Ile | Ile | Leu | Cys | Cys | Asp | Asp | Glu | Arg | Tyr | Lys | Arg |
|     |     |     |     | 325 |     |     |     |     | 330 |     |     |     |     | 335 |     |
| Pro | Pro | Ile | Leu | Gly | Gln | Thr | Val | Pro | Cys | Ser | Thr | Thr | Thr | Ile | Asn |
|     |     |     | 340 |     |     |     |     | 345 |     |     |     |     | 350 |     |     |
| Gly | Ser | Thr | His | Val | Leu | Arg | Asp | Thr | Val | Glu | Cys | Gly | Gly | Gln | Trp |
|     |     | 355 |     |     |     |     | 360 |     |     |     |     | 365 |     |     |     |
| Glu | Ser | Arg | Cys | His | Leu | Thr | Ala | Thr | Ser | Pro | Leu | Val | Ala | Ala | Gln |
|     | 370 |     |     |     |     | 375 |     |     |     |     | 380 |     |     |     |     |
| Pro | Val | Ile | Arg | Arg | Pro | Gln | Asp | Asn | Asp | Leu | Glu | Asp | Ser | Cys | Ser |
| 385 |     |     |     |     | 390 |     |     |     |     | 395 |     |     |     |     | 400 |
| Leu | Lys | Arg | Ser | Gln | Ser |     |     |     |     |     |     |     |     |     |     |
|     |     |     |     | 405 |     |     |     |     |     |     |     |     |     |     |     |

( 2 ) INFORMATION FOR SEQ ID NO:5:

( i ) SEQUENCE CHARACTERISTICS:
        ( A ) LENGTH: 536 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: N ( i v ) ANTI-SENSE: N ( v i ) ORIGINAL SOURCE:
    ( F ) TISSUE TYPE: brain ( v i i ) IMMEDIATE SOURCE:
    ( A ) LIBRARY: human brain
    ( B ) CLONE: S10 PCR ( i x ) FEATURE:
    ( A ) NAME/KEY: CDS
    ( B ) LOCATION: 1..534
    ( D ) OTHER INFORMATION:

( x i ) SEQUENCE DESCRIPTION: SEQ ID NO:5:

```
TTG GTC TAT AGG AAC AAG ATG ACC CCT CTG CGC ATC GCA TTA ATG CTG    48
Leu Val Tyr Arg Asn Lys Met Thr Pro Leu Arg Ile Ala Leu Met Leu
 1               5                  10                  15

GGA GGC TGC TGG GTC ATC CCC ACG TTT ATT TCT TTT CTC CCT ATA ATG    96
Gly Gly Cys Trp Val Ile Pro Thr Phe Ile Ser Phe Leu Pro Ile Met
            20                  25                  30

CAA GGC TGG AAT AAC ATT GGC ATA ATT GAT TTG ATA GAA AAG AGG AAG   144
Gln Gly Trp Asn Asn Ile Gly Ile Ile Asp Leu Ile Glu Lys Arg Lys
        35                  40                  45

TTC AAC CAG AAC TCT AAC TCT ACG TAC TGT GTC TTC ATG GTC AAC AAG   192
Phe Asn Gln Asn Ser Asn Ser Thr Tyr Cys Val Phe Met Val Asn Lys
    50                  55                  60

CCC TAC GCC ATC ACC TGC TCT GTG GTG GCC TTC TAC ATC CCA TTT CTC   240
Pro Tyr Ala Ile Thr Cys Ser Val Val Ala Phe Tyr Ile Pro Phe Leu
65                  70                  75                  80

CTC ATG GTG CTG GCC TAT TAC CGC ATC TAT GTC ACA GCT AAG GAG CAT   288
Leu Met Val Leu Ala Tyr Tyr Arg Ile Tyr Val Thr Ala Lys Glu His
                85                  90                  95

GCC CAT CAG ATC CAG ATG TTA CAA CGG GCA GGA GCC TCC TCC GAG AGC   336
Ala His Gln Ile Gln Met Leu Gln Arg Ala Gly Ala Ser Ser Glu Ser
            100                 105                 110

AGG CCT CAG TCG GCA GAC CAG CAT AGC ACT CAT CCG ATG AGG ACA GAG   384
Arg Pro Gln Ser Ala Asp Gln His Ser Thr His Pro Met Arg Thr Glu
        115                 120                 125

ACC AAA GCA GCC AAG ACC CTG TGC ATC ATC ATG GGT TGC TTC TGC CTC   432
Thr Lys Ala Ala Lys Thr Leu Cys Ile Ile Met Gly Cys Phe Cys Leu
    130                 135                 140

TGC TGG GCA CCA TTC TTT GTC ACC AAT ATT GTG GAT CCT TTC ATA GAC   480
Cys Trp Ala Pro Phe Phe Val Thr Asn Ile Val Asp Pro Phe Ile Asp
145                 150                 155                 160

TAC ACT GTC CCT GGG CAG GTG TGG ACT GCT TTC CTC TGG CTC GGC TAT   528
Tyr Thr Val Pro Gly Gln Val Trp Thr Ala Phe Leu Trp Leu Gly Tyr
                165                 170                 175

ATC AAT TC                                                        536
Ile Asn
```

( 2 ) INFORMATION FOR SEQ ID NO:6:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Leu Val Tyr Arg Asn Lys Met Thr Pro Leu Arg Ile Ala Leu Met Leu
 1               5                  10                  15
```

```
Gly Gly Cys Trp Val Ile Pro Thr Phe Ile Ser Phe Leu Pro Ile Met
        20                  25                  30
Gln Gly Trp Asn Asn Ile Gly Ile Ile Asp Leu Ile Glu Lys Arg Lys
            35              40                  45
Phe Asn Gln Asn Ser Asn Ser Thr Tyr Cys Val Phe Met Val Asn Lys
        50              55                  60
Pro Tyr Ala Ile Thr Cys Ser Val Val Ala Phe Tyr Ile Pro Phe Leu
65                  70                  75                      80
Leu Met Val Leu Ala Tyr Tyr Arg Ile Tyr Val Thr Ala Lys Glu His
                85              90                      95
Ala His Gln Ile Gln Met Leu Gln Arg Ala Gly Ala Ser Ser Glu Ser
            100             105                 110
Arg Pro Gln Ser Ala Asp Gln His Ser Thr His Pro Met Arg Thr Glu
            115             120                 125
Thr Lys Ala Ala Lys Thr Leu Cys Ile Ile Met Gly Cys Phe Cys Leu
    130             135                 140
Cys Trp Ala Pro Phe Phe Val Thr Asn Ile Val Asp Pro Phe Ile Asp
145             150                 155                     160
Tyr Thr Val Pro Gly Gln Val Trp Thr Ala Phe Leu Trp Leu Gly Tyr
            165                 170                 175
Ile Asn
```

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: modified_base
        ( B ) LOCATION: 14

( i x ) FEATURE:
        ( A ) NAME/KEY: modified_base
        ( B ) LOCATION: 20

( x i ) SEQUENCE DESCRIPTION: SEQ ID NO:7:

TGGAATTCTG YGYAATHKCA CTGGAYMGST A            31

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: modified_base
        ( B ) LOCATION: 4

( i x ) FEATURE:
    ( A ) NAME/KEY: modified_base
    ( B ) LOCATION: 7

( i x ) FEATURE:
    ( A ) NAME/KEY: modified_base
    ( B ) LOCATION: 9..10

( i x ) FEATURE:
    ( A ) NAME/KEY: modified_base
    ( B ) LOCATION: 13

( i x ) FEATURE:
    ( A ) NAME/KEY: modified_base
    ( B ) LOCATION: 25

( x i ) SEQUENCE DESCRIPTION: SEQ ID NO:8:

CATAAVARAA ARAGGDATRW ARAAAGC 27

( 2 ) INFORMATION FOR SEQ ID NO:9:

( i ) SEQUENCE CHARACTERISTICS:
    ( A ) LENGTH: 460 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( B ) CLONE: 5HT1C ( x i ) SEQUENCE DESCRIPTION: SEQ ID NO:9:

| Met | Val | Asn | Leu | Gly | Asn | Ala | Val | Arg | Ser | Leu | Leu | Met | His | Leu | Ile |
| 1 | | | | 5 | | | | | 10 | | | | | 15 | |
| Gly | Leu | Leu | Val | Trp | Gln | Phe | Asp | Ile | Ser | Ile | Ser | Pro | Val | Ala | Ala |
| | | | 20 | | | | | 25 | | | | | 30 | | |
| Ile | Val | Thr | Asp | Thr | Phe | Asn | Ser | Ser | Asp | Gly | Gly | Arg | Leu | Phe | Gln |
| | | | 35 | | | | | 40 | | | | | 45 | | |
| Phe | Pro | Asp | Gly | Val | Gln | Asn | Trp | Pro | Ala | Leu | Ser | Ile | Val | Val | Ile |
| | 50 | | | | | 55 | | | | | | 60 | | | |
| Ile | Ile | Met | Thr | Ile | Gly | Gly | Asn | Ile | Leu | Val | Ile | Met | Ala | Val | Ser |
| 65 | | | | | 70 | | | | | 75 | | | | | 80 |
| Met | Glu | Lys | Lys | Leu | His | Asn | Ala | Thr | Asn | Tyr | Phe | Leu | Met | Ser | Leu |
| | | | | 85 | | | | | 90 | | | | | 95 | |
| Ala | Ile | Ala | Asp | Met | Leu | Val | Gly | Leu | Leu | Val | Met | Pro | Leu | Ser | Leu |
| | | | 100 | | | | | 105 | | | | | 110 | | |
| Leu | Ala | Ile | Leu | Tyr | Asp | Tyr | Val | Trp | Pro | Leu | Pro | Arg | Tyr | Leu | Cys |
| | | | 115 | | | | | 120 | | | | | 125 | | |
| Pro | Val | Trp | Ile | Ser | Leu | Asp | Val | Leu | Phe | Ser | Thr | Ala | Ser | Ile | Met |
| | 130 | | | | | 135 | | | | | | 140 | | | |
| His | Leu | Cys | Ala | Ile | Ser | Leu | Asp | Arg | Tyr | Val | Ala | Ile | Arg | Asn | Pro |
| 145 | | | | | 150 | | | | | 155 | | | | | 160 |
| Ile | Glu | His | Ser | Arg | Phe | Asn | Ser | Arg | Thr | Lys | Ala | Ile | Met | Lys | Ile |
| | | | | 165 | | | | | 170 | | | | | 175 | |
| Ala | Ile | Val | Trp | Ala | Ile | Ser | Ile | Gly | Val | Ser | Val | Pro | Ile | Pro | Val |
| | | | 180 | | | | | 185 | | | | | 190 | | |
| Ile | Gly | Leu | Arg | Asp | Glu | Ser | Lys | Val | Phe | Val | Asn | Asn | Thr | Thr | Cys |
| | | | 195 | | | | | 200 | | | | | 205 | | |
| Val | Leu | Asn | Asp | Pro | Asn | Phe | Val | Leu | Ile | Gly | Ser | Phe | Val | Ala | Phe |
| | 210 | | | | | 215 | | | | | | 220 | | | |
| Phe | Ile | Pro | Leu | Thr | Ile | Met | Val | Ile | Thr | Tyr | Phe | Leu | Thr | Ile | Tyr |

-continued

```
            225                     230                     235                     240
       Val  Leu  Arg  Arg  Gln  Thr  Leu  Met  Leu  Leu  Arg  Gly  His  Thr  Glu  Glu
                           245                      250                     255
       Glu  Leu  Ala  Asn  Met  Ser  Leu  Asn  Phe  Leu  Asn  Cys  Cys  Cys  Lys  Lys
                           260                      265                     270
       Asn  Gly  Gly  Glu  Glu  Glu  Asn  Ala  Pro  Asn  Pro  Asn  Pro  Asp  Gln  Lys
                 275                           280                     285
       Pro  Arg  Arg  Lys  Lys  Lys  Glu  Lys  Arg  Pro  Arg  Gly  Thr  Met  Gln  Ala
                 290                           295                     300
       Ile  Asn  Asn  Glu  Lys  Lys  Ala  Ser  Lys  Val  Leu  Gly  Ile  Val  Phe  Phe
       305                           310                      315                     320
       Val  Phe  Leu  Ile  Met  Trp  Cys  Pro  Phe  Phe  Ile  Thr  Asn  Ile  Leu  Ser
                           325                      330                     335
       Val  Leu  Cys  Gly  Lys  Ala  Cys  Asn  Gln  Lys  Leu  Met  Glu  Lys  Leu  Leu
                      340                           345                     350
       Asn  Val  Phe  Val  Trp  Ile  Gly  Tyr  Val  Cys  Ser  Gly  Ile  Asn  Pro  Leu
                      355                           360                     365
       Val  Tyr  Thr  Leu  Phe  Asn  Lys  Ile  Tyr  Arg  Arg  Ala  Phe  Ser  Lys  Tyr
                 370                           375                     380
       Leu  Arg  Cys  Asp  Tyr  Lys  Pro  Asp  Lys  Lys  Pro  Pro  Val  Arg  Gln  Ile
       385                           390                      395                     400
       Pro  Arg  Val  Ala  Ala  Thr  Ala  Leu  Ser  Gly  Arg  Glu  Leu  Asn  Val  Asn
                           405                      410                     415
            Ile  Tyr  Arg  His  Thr  Asn  Glu  Arg  Val  Ala  Arg  Lys  Ala  Asn  Asp  Pro
                                420                           425                     430
       Glu  Pro  Gly  Ile  Glu  Met  Gln  Val  Glu  Asn  Leu  Glu  Leu  Pro  Val  Asn
                      435                           440                     445
       Pro  Ser  Asn  Val  Val  Ser  Glu  Arg  Ile  Ser  Ser  Val
                 450                           455                     460
```

( 2 ) INFORMATION FOR SEQ ID NO:10:

( i ) SEQUENCE CHARACTERISTICS:
        ( A ) LENGTH: 359 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: HIST2

( x i ) SEQUENCE DESCRIPTION: SEQ ID NO:10:

```
       Met  Ile  Ser  Asn  Gly  Thr  Gly  Ser  Ser  Phe  Cys  Leu  Asp  Ser  Pro  Pro
       1                      5                           10                      15
       Cys  Arg  Ile  Thr  Val  Ser  Val  Val  Leu  Thr  Val  Leu  Ile  Leu  Ile  Thr
                      20                           25                      30
       Ile  Ala  Gly  Asn  Val  Val  Val  Cys  Leu  Ala  Val  Gly  Leu  Asn  Arg  Arg
                 35                           40                      45
       Leu  Arg  Ser  Leu  Thr  Asn  Cys  Phe  Ile  Val  Ser  Leu  Ala  Ile  Thr  Asp
                 50                           55                      60
       Leu  Leu  Leu  Gly  Leu  Leu  Val  Leu  Pro  Phe  Ser  Ala  Phe  Tyr  Gln  Leu
       65                           70                      75                      80
       Ser  Cys  Arg  Trp  Ser  Phe  Gly  Lys  Val  Phe  Cys  Asn  Ile  Tyr  Thr  Ser
                           85                           90                      95
       Leu  Asp  Val  Met  Leu  Cys  Thr  Ala  Ser  Ile  Leu  Asn  Leu  Phe  Met  Ile
```

|     |     | 100 |     |     |     | 105 |     |     |     | 110 |     |     |     |
|-----|-----|-----|-----|-----|-----|-----|-----|-----|-----|-----|-----|-----|-----|

Ser Leu Asp Arg Tyr Cys Ala Val Thr Asp Pro Leu Arg Tyr Pro Val
        115                 120                 125

Leu Ile Thr Pro Val Arg Val Ala Val Ser Leu Val Leu Ile Trp Val
    130                 135                 140

Ile Ser Ile Thr Leu Ser Phe Leu Ser Ile His Leu Gly Trp Asn Ser
145                 150                 155                 160

Arg Asn Glu Thr Ser Ser Phe Asn His Thr Ile Pro Lys Cys Lys Val
                165                 170                 175

Gln Val Asn Leu Val Tyr Gly Leu Val Asp Gly Leu Val Thr Phe Tyr
            180                 185                 190

Leu Pro Leu Leu Val Met Cys Ile Thr Tyr Tyr Arg Ile Phe Lys Ile
        195                 200                 205

Ala Arg Asp Gln Ala Lys Arg Ile His His Met Gly Ser Trp Lys Ala
    210                 215                 220

Ala Thr Ile Gly Glu His Lys Ala Thr Val Thr Leu Ala Ala Val Met
225                 230                 235                 240

Gly Ala Phe Ile Ile Cys Trp Phe Pro Tyr Phe Thr Val Phe Val Tyr
                245                 250                 255

Arg Gly Leu Lys Gly Asp Asp Ala Ile Asn Glu Ala Phe Glu Ala Val
            260                 265                 270

Val Leu Trp Leu Gly Tyr Ala Asn Ser Ala Leu Asn Pro Ile Leu Tyr
        275                 280                 285

Ala Thr Leu Asn Arg Asp Phe Arg Thr Ala Tyr Gln Gln Leu Phe Arg
    290                 295                 300

Cys Arg Pro Ala Ser His Asn Ala Gln Glu Thr Ser Leu Arg Ser Asn
305                 310                 315                 320

Ser Ser Gln Leu Ala Arg Asn Gln Ser Arg Glu Pro Met Arg Gln Glu
                325                 330                 335

Glu Lys Pro Leu Lys Leu Gln Val Trp Ser Gly Thr Glu Val Thr Ala
            340                 345                 350

Pro Arg Gly Ala Thr Asp Arg
        355

( 2 ) INFORMATION FOR SEQ ID NO:11:

( i ) SEQUENCE CHARACTERISTICS:
        ( A ) LENGTH: 471 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: 5-HT2

( x i ) SEQUENCE DESCRIPTION: SEQ ID NO:11:

Met Glu Ile Leu Cys Glu Asp Asn Ile Ser Leu Ser Ser Ile Pro Asn
1               5                   10                  15

Ser Leu Met Gln Leu Gly Asp Gly Pro Arg Leu Tyr His Asn Asp Phe
            20                  25                  30

Asn Ser Arg Asp Ala Asn Thr Ser Glu Ala Ser Asn Trp Thr Ile Asp
        35                  40                  45

Ala Glu Asn Arg Thr Asn Leu Ser Cys Glu Gly Tyr Leu Pro Pro Thr
    50                  55                  60

Cys Leu Ser Ile Leu His Leu Gln Glu Lys Asn Trp Ser Ala Leu Leu

|     |     |     |     | 65  |     |     |     | 70  |     |     |     | 75  |     |     |     | 80  |
| --- | --- | --- | --- | --- | --- | --- | --- | --- | --- | --- | --- | --- | --- | --- | --- | --- |
| Thr | Thr | Val | Val | Ile | Ile | Leu | Thr | Ile | Ala | Gly | Asn | Ile | Leu | Val | Ile |
|     |     |     |     | 85  |     |     |     | 90  |     |     |     | 95  |     |     |     |
| Met | Ala | Val | Ser | Leu | Glu | Lys | Lys | Leu | Gln | Asn | Ala | Thr | Asn | Tyr | Phe |
|     |     |     |     | 100 |     |     |     | 105 |     |     |     | 110 |     |     |     |
| Leu | Met | Ser | Leu | Ala | Ile | Ala | Asp | Met | Leu | Leu | Gly | Phe | Leu | Val | Met |
|     |     |     |     | 115 |     |     |     | 120 |     |     |     | 125 |     |     |     |
| Pro | Val | Ser | Met | Leu | Thr | Ile | Leu | Tyr | Gly | Tyr | Arg | Trp | Pro | Leu | Pro |
|     |     |     |     | 130 |     |     |     | 135 |     |     |     | 140 |     |     |     |
| Ser | Lys | Leu | Cys | Ala | Ile | Trp | Ile | Tyr | Leu | Asp | Val | Leu | Phe | Ser | Thr |
|     |     |     |     | 145 |     |     |     | 150 |     |     |     | 155 |     |     | 160 |
| Ala | Ser | Ile | Met | His | Leu | Cys | Ala | Ile | Ser | Leu | Asp | Arg | Tyr | Val | Ala |
|     |     |     |     |     |     | 165 |     |     |     | 170 |     |     |     | 175 |     |
| Ile | Gln | Asn | Pro | Ile | His | His | Ser | Arg | Phe | Asn | Ser | Arg | Thr | Lys | Ala |
|     |     |     |     | 180 |     |     |     | 185 |     |     |     | 190 |     |     |     |
| Phe | Leu | Lys | Ile | Ile | Ala | Val | Trp | Thr | Ile | Ser | Val | Gly | Ile | Ser | Met |
|     |     |     |     | 195 |     |     |     | 200 |     |     |     | 205 |     |     |     |
| Pro | Ile | Pro | Val | Phe | Gly | Leu | Gln | Asp | Ser | Lys | Val | Phe | Lys | Glu |
|     |     |     |     | 210 |     |     |     | 215 |     |     |     | 220 |     |     |
| Gly | Ser | Cys | Leu | Leu | Ala | Asp | Asp | Asn | Phe | Val | Leu | Ile | Gly | Ser | Phe |
| 225 |     |     |     |     |     | 230 |     |     |     | 235 |     |     |     |     | 240 |
| Val | Ala | Phe | Phe | Ile | Pro | Leu | Thr | Ile | Met | Val | Ile | Thr | Tyr | Phe | Leu |
|     |     |     |     |     | 245 |     |     |     | 250 |     |     |     | 255 |     |     |
| Thr | Ile | Lys | Ser | Leu | Gln | Lys | Glu | Ala | Thr | Leu | Cys | Val | Ser | Asp | Leu |
|     |     |     | 260 |     |     |     | 265 |     |     |     | 270 |     |     |     |     |
| Ser | Thr | Arg | Ala | Lys | Leu | Ala | Ser | Phe | Ser | Phe | Leu | Pro | Gln | Ser | Ser |
|     |     | 275 |     |     |     | 280 |     |     |     | 285 |     |     |     |     |     |
| Leu | Ser | Ser | Glu | Lys | Leu | Phe | Gln | Arg | Ser | Ile | His | Arg | Glu | Pro | Gly |
|     | 290 |     |     |     | 295 |     |     |     |     | 300 |     |     |     |     |     |
| Ser | Tyr | Ala | Gly | Arg | Arg | Thr | Met | Gln | Ser | Ile | Ser | Asn | Glu | Gln | Lys |
| 305 |     |     |     | 310 |     |     |     | 315 |     |     |     |     |     |     | 320 |
| Ala | Cys | Lys | Val | Leu | Gly | Ile | Val | Phe | Phe | Leu | Phe | Val | Val | Met | Trp |
|     |     |     |     | 325 |     |     |     | 330 |     |     |     |     |     | 335 |     |
| Cys | Pro | Phe | Phe | Ile | Thr | Asn | Ile | Met | Ala | Val | Ile | Cys | Lys | Glu | Ser |
|     |     |     | 340 |     |     |     |     | 345 |     |     |     |     | 350 |     |     |
| Cys | Asn | Glu | Asn | Val | Ile | Gly | Ala | Leu | Leu | Asn | Val | Phe | Val | Trp | Ile |
|     |     | 355 |     |     |     |     | 360 |     |     |     |     | 365 |     |     |     |
| Gly | Tyr | Leu | Ser | Ser | Ala | Val | Asn | Pro | Leu | Val | Tyr | Thr | Leu | Phe | Asn |
|     | 370 |     |     |     |     | 375 |     |     |     |     | 380 |     |     |     |     |
| Lys | Thr | Tyr | Arg | Ser | Ala | Phe | Ser | Arg | Tyr | Ile | Gln | Cys | Gln | Tyr | Lys |
| 385 |     |     |     |     | 390 |     |     |     |     | 395 |     |     |     |     | 400 |
| Glu | Asn | Arg | Lys | Pro | Leu | Gln | Leu | Ile | Leu | Val | Asn | Thr | Ile | Pro | Ala |
|     |     |     |     | 405 |     |     |     |     | 410 |     |     |     |     | 415 |     |
| Leu | Ala | Tyr | Lys | Ser | Ser | Gln | Leu | Gln | Val | Gly | Gln | Lys | Lys | Asn | Ser |
|     |     |     |     | 420 |     |     |     |     | 425 |     |     |     | 430 |     |     |
| Gln | Glu | Asp | Ala | Glu | Gln | Thr | Val | Asp | Asp | Cys | Ser | Met | Val | Thr | Leu |
|     |     | 435 |     |     |     |     | 440 |     |     |     |     | 445 |     |     |     |
| Gly | Lys | Gln | Gln | Ser | Glu | Glu | Asn | Cys | Thr | Asp | Asn | Ile | Glu | Thr | Val |
|     |     | 450 |     |     |     | 455 |     |     |     |     | 460 |     |     |     |     |
| Asn | Glu | Lys | Val | Ser | Cys | Val |
| 465 |     |     |     |     | 470 |     |

( 2 ) INFORMATION FOR SEQ ID NO:12:

(i) SEQUENCE CHARACTERISTICS:
 (A) LENGTH: 422 amino acids
 (B) TYPE: amino acid
 (C) STRANDEDNESS: single
 (D) TOPOLOGY: linear (ii) MOLECULE TYPE: protein (vii) IMMEDIATE SOURCE:
 (B) CLONE: HP78

(xi) SEQUENCE DESCRIPTION: SEQ ID NO:12:

```
Met Met Asp Val Asn Ser Ser Gly Arg Pro Asp Leu Tyr Gly His Leu
1               5                   10                  15

Arg Ser Phe Leu Leu Pro Glu Val Gly Arg Gly Glu Val Thr Ala Ser
            20                  25                  30

Pro Ala Pro Thr Trp Asp Ala Pro Pro Asp Asn Ala Ser Gly Cys Gly
            35                  40                  45

Glu Gln Ile Asn Tyr Gly Arg Val Glu Lys Val Val Ile Gly Ser Ile
        50                  55                  60

Leu Thr Leu Ile Thr Leu Leu Thr Ile Ala Gly Asn Cys Leu Val Val
65                  70                  75                  80

Ile Ser Val Cys Phe Val Lys Lys Leu Arg Gln Pro Ser Asn Tyr Leu
                85                  90                  95

Ile Val Ser Leu Ala Leu Ala Asp Leu Ser Val Ala Val Ala Val Met
            100                 105                 110

Pro Phe Val Ser Val Thr Asp Leu Ile Gly Gly Lys Trp Ile Phe Gly
            115                 120                 125

His Phe Phe Cys Asn Val Phe Ile Ala Met Asp Val Met Cys Cys Thr
    130                 135                 140

Ala Ser Ile Met Thr Leu Cys Val Ile Ser Ile Asp Arg Tyr Leu Gly
145                 150                 155                 160

Ile Thr Arg Pro Leu Thr Tyr Pro Val Arg Gln Asn Gly Lys Cys Met
                165                 170                 175

Ala Lys Met Ile Leu Ser Val Trp Leu Leu Ser Ala Ser Ile Thr Leu
            180                 185                 190

Pro Pro Leu Phe Gly Trp Ala Gln Asn Val Asn Asp Asp Lys Val Cys
            195                 200                 205

Leu Ile Ser Gln Asp Phe Gly Tyr Thr Ile Tyr Ser Thr Ala Val Ala
        210                 215                 220

Phe Tyr Ile Pro Met Ser Val Met Leu Phe Met Tyr Tyr Gln Ile Tyr
225                 230                 235                 240

Lys Ala Ala Arg Lys Ser Ala Ala Lys His Lys Phe Pro Gly Phe Pro
                245                 250                 255

Arg Val Glu Pro Asp Ser Val Ile Ala Leu Asn Gly Ile Val Lys Leu
            260                 265                 270

Gln Lys Glu Val Glu Glu Cys Ala Asn Leu Ser Arg Leu Leu Lys His
            275                 280                 285

Glu Arg Lys Asn Ile Ser Ile Phe Lys Arg Glu Gln Lys Ala Ala Thr
    290                 295                 300

Thr Leu Gly Ile Ile Val Gly Ala Phe Thr Val Cys Trp Leu Pro Phe
305                 310                 315                 320

Phe Leu Leu Ser Thr Ala Arg Pro Phe Ile Cys Gly Thr Ser Cys Ser
            325                 330                 335

Cys Ile Pro Leu Trp Val Glu Arg Thr Phe Leu Trp Leu Gly Tyr Ala
            340                 345                 350
```

```
Asn  Ser  Leu  Ile  Asn  Pro  Phe  Ile  Tyr  Ala  Phe  Phe  Asn  Arg  Asp  Leu
          355                      360                     365

Arg  Thr  Thr  Tyr  Arg  Ser  Leu  Leu  Gln  Cys  Gln  Tyr  Arg  Asn  Ile  Asn
     370                      375                     380

Arg  Lys  Leu  Ser  Ala  Ala  Gly  Met  His  Glu  Ala  Leu  Lys  Leu  Ala  Glu
385                      390                     395                          400

Arg  Pro  Glu  Arg  Pro  Glu  Phe  Val  Leu  Gln  Asn  Ala  Asp  Tyr  Cys  Arg
                    405                     410                          415

Lys  Lys  Gly  His  Asp  Ser
               420
```